(12) United States Patent
Wiesner et al.

(10) Patent No.: US 7,060,707 B2
(45) Date of Patent: Jun. 13, 2006

(54) ISOQUINOLINE DERIVATIVES

(75) Inventors: Matthias Wiesner, Seeheim-Jugenheim (DE); Simon Goodman, Griesheim (DE); Horst Kessler, Schwalbach (DE); Georgette Thumshirn, München (DE); Dirk Weber, München (DE); Dirk Gottschling, Senden (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/506,820

(22) PCT Filed: Feb. 7, 2003

(86) PCT No.: PCT/EP03/01248

§ 371 (c)(1), (2), (4) Date: Sep. 7, 2004

(87) PCT Pub. No.: WO03/074512

PCT Pub. Date: Sep. 12, 2003

(65) Prior Publication Data

US 2005/0090525 A1    Apr. 28, 2005

(30) Foreign Application Priority Data

Mar. 6, 2002 (DE) ................. 102 09 692

(51) Int. Cl.
*A61K 31/44* (2006.01)
*C07D 401/02* (2006.01)
(52) U.S. Cl. .................. 514/275; 514/307; 546/147; 544/315
(58) Field of Classification Search ............. 546/147; 544/316; 514/275, 307
See application file for complete search history.

(56) References Cited

U.S. PATENT DOCUMENTS 6,262,069 B1    7/2001    Liebeschuetz et al.
2002/0055522 A1    5/2002    Liebeschuetz et al.

FOREIGN PATENT DOCUMENTS

WO    WO 9911658    3/1999
WO    WO 0076971    12/2000
WO    WO 0105753    1/2001

*Primary Examiner*—Zinna N. Davis
(74) *Attorney, Agent, or Firm*—Miller, White, Zelano, Branigan, P.C.

(57) ABSTRACT

Isoquinoline derivatives of the general formula (I) in which X, Y, Z, $R^1$, $R^2$ and n are as defined in Patent Claim (1), and physiologically acceptable salts or solvates thereof, are integrin inhibitors and can be employed for combating thromboses, cardiac infarction, coronary heart diseases, arteriosclerosis, inflammation, tumors, osteoporosis, infections and restenosis after angioplasty or in pathological processes which are maintained or propagated by angiogenesis.

16 Claims, No Drawings

ISOQUINOLINE DERIVATIVES

The invention relates to compounds of the general formula I

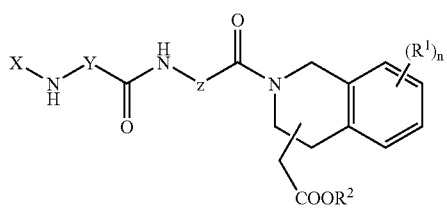

in which

X is H, —C(=NR$^3$)—NHR$^4$ or Het,

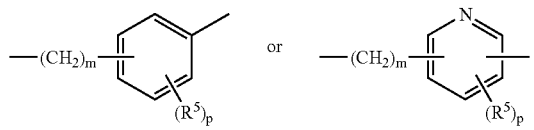

Y is —(CH2)m-,

Z is NH or CH$_2$,

R$^1$ and R$^5$ are each, independently of one another, H, A, OH, OA, arylalkyl, Hal, —CO—A, CN, NO$_2$, NHR$^3$, COOA, COOH, SO$_2$A, CF$_3$ or OCF$_3$, R$^2$ is in each case, independently of the others, H or A, R$^3$ and R$^4$ are each, independently of one another, H, A, —CO—A, NO$_2$ or CN.

A is alkyl having 1–6 carbon atoms, m is 0, 1, 2, 3, 4, 5 or 6, n and p are, independently of one another, 1, 2 or 3, and physiologically acceptable derivatives thereof, in particular salts and solvates thereof.

The invention had the object of finding novel compounds having valuable properties, in particular those which are used for the preparation of medicaments.

It has been found that the compounds of the formula I and salts thereof have very valuable pharmacological properties and are well tolerated. In particular, they act as integrin inhibitors, inhibiting, in particular, the interactions of the αv, β3, β5 or β6 integrin receptors with ligands, such as, for example, the binding of fibrinogen to the integrin receptor.

Integrins belong to the family of heterodimeric class I transmembrane receptors, which play an important role in numerous cell-matrix and cell-cell adhesion processes (Tuckwell et al., 1996, Symp. Soc. Exp. Biol. 47). They can be divided roughly into three classes: the β1 integrins, which are receptors for the extracellular matrix, the β2 integrins, which can be activated on leukocytes and are triggered during inflammatory processes, and the αv integrins which influence the cell response during wound-healing and other pathological processes (Marshall and Hart, 1996, Semin. Cancer Biol. 7, 191). The relative affinity and specificity for ligand binding is determined by the combination of the various α and β sub-units.

The compounds according to the invention exhibit particular effectiveness in the case of integrins αvβ1, αvβ3, αvβ5, αIIbβ3 as well as αvβ6 and αvβ8, preferably of αvβ3, αvβ5 and αvβ6, as well as αIIbβ3.

αvβ6 is a relatively rare integrin (Busk et al., J. Biol. Chem. 1992, 267(9), 5790), which is formed to an increased extent during repair processes in epithelial tissue and which preferably binds the natural matrix molecules fibronectin and tenascin (Wang et al., Am. J. Respir. Cell Mol. Biol. 1996, 15(5), 664). The physiological and pathological functions of αvβ6 are not yet known precisely, but it is assumed that this integrin plays an important role in physiological processes and diseases (for example inflammation, wound healing, tumours) in which epithelial cells are involved. Thus, αvβ6 is expressed on keratinocytes in wounds (Haapasalmi et al., J. Invest. Dermatol. 1996, 106(1), 42), from which it can be assumed that, besides wound-healing processes and inflammation, other pathological events of the skin, such as, for example, psoriasis, bullate pemphigus, dermatitis and erythema and also cystic fibrosis, endometriosis, liver cirrhosis and periodontitis, can also be influenced by agonists or antagonists of the said integrin. Furthermore, αvβ6 plays a role in the respiratory tract epithelium (Weinacker et al., Am. J. Respir. Cell Mol. Biol. 1995, 12(5), 547), and consequently corresponding agonists/antagonists of this integrin could successfully be employed in respiratory tract diseases, such as bronchitis, asthma, lung fibrosis and respiratory tract tumours. Finally, it is known that αvβ6 also plays a role in the intestinal epithelium, which means that the corresponding integrin agonists/antagonists could be used in the treatment of inflammation, tumours and wounds of the gastric/intestinal tract.

It has been found that the compounds of the formula I according to the invention and salts thereof exert, as soluble molecules, an action on cells which carry the said receptor or, if they are bonded to surfaces, are artificial ligands for αvβ6-mediated cell adhesion. In particular, they act as αvβ6 integrin inhibitors, inhibiting, in particular, the interactions of the receptor with other ligands, such as, for example, the binding of fibronectin.

The compounds according to the invention are, in particular, potent inhibitors of the vitronectin receptor αvβ3 and/or potent inhibitors of the αvβ6 receptor.

αvβ3 integrin is expressed on a number of cells, for example endothelial cells, cells of smooth vascular muscles, for example of the aorta, cells for breaking down bone matrix (osteoclasts) or tumour cells.

The action of the compounds according to the invention can be demonstrated, for example, by the method described by J. W. Smith et al. in J. Biol. Chem. 1990, 265, 12267–12271.

B. Felding-Habermann and D. A. Cheresh in Curr. Opin. Cell. Biol. 1993, 5, 864, describe the importance of the integrins as adhesion receptors for a very wide variety of phenomena and syndromes, especially with relation to the vitronectin receptor αvβ3.

The dependence of the occurence of angiogenesis on the interaction between vascular integrins and extracellular matrix proteins has been described by P. C. Brooks, R. A. Clark and D. A. Cheresh in Science 1994, 264, 569–571.

The possibility of inhibiting this interaction and thus initiating apoptosis (programmed cell death) of angiogenic vascular cells by a cyclic peptide has been described by P. C. Brooks, A. M. Montgomery, M. Rosenfeld, R. A. Reisfeld, T. Hu, G. Klier and D. A. Cheresh in Cell 1994, 79,1157–1164. This described, for example, αvβ3 antagonists or antibodies against αvβ3 which cause shrinkage of tumours due to the initiation of apoptosis.

The experimental evidence that the compounds according to the invention also prevent the adhesion of living cells to the corresponding matrix proteins and accordingly also prevent the adhesion of tumour cells to matrix proteins can be provided in a cell adhesion test analogously to the method of F. Mitjans et al., J. Cell Science 1995, 108, 2825–2838.

P. C. Brooks et al. in J. Clin. Invest. 1995, 96, 1815–1822, describe $\alpha_v\beta_3$ antagonists for combating cancer and for the treatment of tumour-induced angiogenic diseases.

The compounds are able to inhibit the binding of metal proteinases to integrins and thus prevent the cells from being able to utilise the enzymatic activity of the proteinase. An example is the possibility of inhibiting the binding of MMP-2-(matrix metalloproteinase 2-) to the vitronectin receptor $\alpha v\beta 3$ by a cyclo-RGD peptide, as described in P. C. Brooks et al., Cell 1996, 85, 683–693.

The compounds of the formula I according to the invention can therefore be employed as medicament active ingredients, in particular for the treatment of tumour diseases, osteoporosis, osteolytic diseases and for the suppression of angiogenesis.

Compounds of the formula I which block the interaction of integrin receptors and ligands, such as, for example, of fibrinogen to the fibrinogen receptor (glycoprotein IIb/IIIa), prevent, as GPIIb/IIIa antagonists, the spread of tumour cells by metastasis. This is confirmed by the following observations:

The spread of tumour cells from a local tumour into the vascular system takes place through the formation of microaggregates (microthrombi) through the interaction of the tumour cells with blood platelets. The tumour cells are screened by the protection in the microaggregate and are not recognised by the cells of the immune system. The microaggregates can attach themselves to vascular walls, simplifying further penetration of tumour cells into the tissue. Since the formation of the microthrombi is promoted by fibrinogen binding to the fibrinogen receptors on activated blood platelets, the GPIIb/IIIa antagonists can be regarded as effective metastasis inhibitors.

Besides the binding of fibrinogen, fibronectin and von Willebrand factor to the fibrinogen receptor of the blood platelets, compounds of the formula I also inhibit the binding of further adhesive proteins, such as vitronectin, collagen and laminin, to the corresponding receptors on the surface of various types of cell. In particular, they prevent the formation of blood-platelet thrombi and can therefore be employed for the treatment of thromboses, apoplexia, cardiac infarction, inflammation and arteriosclerosis.

The thrombocyte aggregation-inhibiting action can be demonstrated in vitro by the method of Born (Nature 1962, 4832, 927–929).

A measure of the take-up of a medicament active ingredient into an organism is its bioavailability.

If the medicament active ingredient is administered to the organism intravenously in the form of an injection solution, its absolute bioavailability, i.e. the proportion of the pharmaceutical species which is unchanged in the systemic blood, i.e. enters the general circulation, is 100%.

On oral administration of a therapeutic active ingredient, the active ingredient is generally present in the formulation in the form of a solid and must therefore first dissolve in order that it can overcome the entry barriers, for example the gastrointestinal tract, the oral mucous membrane, nasal membranes or the skin, in particular the stratum corneum, and can be absorbed by the body. Pharmacokinetic data, i.e. on the bioavailability, can be obtained analogously to the method of J. Shaffer et al., J. Pharm. Sciences, 1999, 88, 313–318.

The invention relates to compounds of the formula I according to Claim 1 and physiologically acceptable salts and/or solvates thereof as therapeutic active ingredients.

The invention accordingly relates to compounds of the formula I according to Claim 1 and physiologically acceptable salts and/or solvates thereof as integrin inhibitors.

The invention relates to compounds of the formula I according to Claim 1 and physiologically acceptable salts and/or solvates thereof for use in combating diseases.

The compounds of the formula I can be employed as medicament active ingredients in human and veterinary medicine, in particular for the prophylaxis and/or therapy of circulatory diseases, thromboses, cardiac infarction, arteriosclerosis, apoplexia, angina pectoris, tumour diseases, such as tumour growth or tumour metastasis, osteolytic diseases, such as osteoporosis, pathologically angiogenic diseases, such as, for example, inflammation, ophthalmological diseases, diabetic retinopathy, macular degeneration, myopia, ocular histoplasmosis, rheumatic arthritis, osteoarthritis, rubeotic glaucoma, ulcerative colitis, Crohn's disease, atherosclerosis, psoriasis, bullate pemphigus, dermatitis, erythema, lung fibrosis, cystic fibrosis, endometriosis, liver cirrhosis, periodontitis, restenosis after angioplasty, multiple sclerosis, viral infections, bacterial infections, fungal infections, in acute renal failure and in wound healing for supporting the healing process.

The compounds of the formula I can be employed as antimicrobially active substances in operations where biomaterials, implants, catheters or cardiac pacemakers are used. They have an antiseptic action here. The efficacy of the antimicrobial activity can be demonstrated by the method described by P. Valentin-Weigund et. al. in Infection and Immunity, 1988, 2851–2855.

Since the compounds of the formula I are inhibitors of fibrinogen binding and are thus ligands of the fibrinogen receptors on blood platelets, they can be used in vivo as diagnostic agents for the detection and localisation of thrombi in vascular systems if they are substituted, for example, by a radioactive or UV-detectable radical.

The compounds of the formula I, as inhibitors of fibrinogen binding, can also be used as effective aids for the study of the metabolism of blood platelets in various stages of activation or of intracellular signal mechanisms of the fibrinogen receptor. The detectable unit of a label to be incorporated, for example isotope labelling by $^3H$, allows the said mechanisms to be studied after binding to the receptor.

The following abbreviations are used below:
Ac acetyl
Aza-Gly H$_2$N—NH—COOH
BOC tert-butoxycarbonyl
CBZ or Z benzyloxycarbonyl
DCCI dicyclohexylcarbodiimide
DCM dichloromethane
DIPEA diisopropylethylamine
DMF dimethylformamide
DMSO dimethyl sulfoxide
EDCI N-ethyl-N,N'-(dimethylaminopropyl)carbodiimide
Et ethyl
Fmoc 9-fluorenylmethoxycarbonyl
Gly glycine
Gua guanidine
HATU O-(7-azabenzotriazol-1-yl)-N,N,N',N'-tetramethyluronium hexafluorophosphate
HOBt 1-hydroxybenzotriazole
Me methyl
MBHA 4-methylbenzhydrylamine Mtr 4-methoxy-2,3,6-trimethylphenylsulfonyl
NMP N-methylpyrrolidone
NMR nuclear magnetic resonance
HONSu N-hydroxysuccinimide
OBzl benzyl ester
OtBu tert-butyl ester
Oct octanoyl
OMe methyl ester
OEt ethyl ester
Pbf 2,2,4,6,7-pentamethyldihydrobenzofuran-5-sulfonyl
β-Phe β-phenylalanine
POA phenoxyacetyl
Pyr pyridine
$R_f$ value retention factor
RP Reversed Phase
RT retention time
Sal salicyloyl
TBTU O-(1H-benzotriazol-1-yl)-N,N,N',N'-tetramethyluronium tetra-fluoroborate
TFA trifluoroacetic acid
Thiqu 1,2,3,4-tetrahydroisoquinoline
Trt trityl (triphenylmethyl).

The compounds of the formula I have at least one centre of chirality and can therefore occur in a number of stereoisomeric forms. All these forms (for example D and L forms) and mixtures thereof (for example the DL forms) are included in the formula I.

The compounds according to Claim 1 according to the invention also include so-called prodrug derivatives, i.e. compounds of the formula I which have been modified with, for example, alkyl or acyl groups, sugars or oligopeptides and which are rapidly cleaved in the organism to give the effective compounds according to the invention.

These also include biodegradable polymer derivatives of the compounds according to the invention, as described, for example, in Int. J. Pharm. 1995, 115, 61–67.

The compounds according to Claim 1 according to the invention also include derivatives of the compounds of the formula I whose carboxyl group has been converted into a pharmaceutically acceptable metabolically labile ester or an amide thereof.

Furthermore, free amino groups or free hydroxyl groups as substituents of compounds of the formula I may have been provided with corresponding protecting groups.

The term solvates of the compounds of the formula I is taken to mean adductions of inert solvent molecules onto the compounds of the formula I which form owing to their mutual attractive force. Solvates are, for example, monohydrates or dihydrates or addition compounds with alcohols, such as, for example, with methanol or ethanol.

The invention furthermore relates to a process for the preparation of compounds of the formula I according to claim 1 and salts thereof, characterised in that a) a compound of the formula II

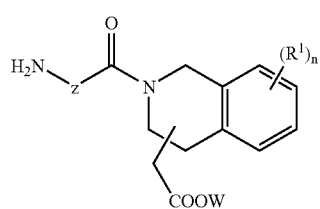

II in which Z, $R^1$ and n are as defined above, and W is a conventional protecting group or a solid phase used in peptide chemistry,
is reacted with a compound of the formula III

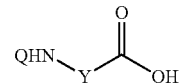

III in which Y is as defined above, and Q is a suitable protecting group or Het, in the presence of a condensing agent, such as, for example, HATU,
and the protecting groups and/or the solid phase are subsequently removed,
and, where appropriate, the resultant product is, if Q as protecting group is removed, reacted with a suitable guanyl compound, such as, for example, N,N'-bis-BOC-1-guanylpyrazole, and, if desired, the remaining protecting groups and/or the solid phase are removed, or b) a compound of the formula I is liberated from one of its functional derivatives by treatment with a solvolysing or hydrogenolysing agent,
and/or in that a basic or acidic compound of the formula I is converted into one of its salts by treatment with an acid or base.

Throughout the invention, all radicals which occur more than once, such as, for example, $R^1$, may be identical or different, i.e. are independent of one another.

In the above formulae, A is alkyl, is linear or branched, and has from 1 to 6, preferably 1, 2, 3, 4, 5 or 6 carbon atoms. A is preferably methyl, furthermore ethyl, isopropyl, n-propyl, n-butyl, isobutyl, sec-butyl or tert-butyl, furthermore also n-pentyl, 1-, 2- or 3-methylbutyl, 1,1-, 1,2- or 2,2-dimethylpropyl, 1-ethylpropyl, hexyl, 1-, 2-, 3- or4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl. A is particularly preferably methyl.

The term "protecting group" preferably denotes acetyl, propionyl, butyryl, phenylacetyl, benzoyl, tolyl, POA, methoxycarbonyl, ethoxycarbonyl, 2,2,2-trichloroethoxycarbonyl, BOC, 2-iodoethoxycarbonyl CBZ ("carbobenzoxy"), 4-methoxybenzyloxycarbonyl, Fmoc, Mtr or benzyl, particularly preferably Fmoc.

Arylalkyl is preferably benzyl, phenylethyl, phenylpropyl or naphthylmethyl, particularly preferably benzyl.

Hal is preferably F, Cl or Br.

Het is a monocyclic or bicyclic aromatic or saturated radical having up to three heteroatoms, preferably a saturated, partially or completely unsaturated monocyclic or bicyclic heterocyclic radical having from 5 to 10 ring members, where 1 or 2 N and/or 1 or 2 S or O atoms may be present and the heterocyclic radical may be monosubstituted or disubstituted by CN, Hal, OH, OA, $CF_3$, A, $NO_2$ or $OCF_3$.

Het is preferably substituted or unsubstituted 2- or 3-furyl, 2- or 3-thienyl, 1-, 2- or 3-pyrrolyl, 1-, 2-, 4- or 5-imidazolyl, 3-, 4- or 5-pyrazolyl, 2-, 4- or 5-oxazolyl, 3-, 4- or 5-isoxazolyl, 2-, 4- or 5-thiazolyl, 3-, 4- or 5 -isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -4- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-1H-indolyl, 1-, 2-, 4- or 5-benzimidazolyl, 1-, 3-, 4-, 5-, 6-, or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6-, or 7-benzisothiazolyl, 4-, 5-, 6- or 7-benz-2,1,3-oxadiazolyl, 1-, 2-, 3-, 4-, 5-, 6-, 7-, or 8-quinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl. The heterocyclic radicals may also be partially or fully hydrogenated. Het may thus also be 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, 4- or -5-pyrrolyl, 1-, 2- or 3-pyrrolidinyl, tetrahydro-1-, -2- or -3-pyrollyl, tetrahydro-1-, -2- or -4-imidazolyl, 2,3-dihydro-1, -2-, -3-, 4-, -5-, -6- or -7-1H-indolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, 4-, -5- or -6-pyridyl, 1,2,3,6-tetrahydro-1-, -2-, -3-, 4-, -5- or -6-pyridyl, 1-, 2-, 3- or 4-piperidinyl, 1-, 2-, 3- or 4-azepanyl, 2-, 3- or 4-morpholinyl, tetrahydro -2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolinyl, 1,2,3,4-tetrahydro-1-, -2-, -3-,-4-, -5-,-6-, -7- or -8-isoquinolinyl. Het is particularly preferably methylpyridyl, in particular 4-methylpyridin-2-yl, pyridin-2-yl, pyrimidin-2-yl, imidazol-2-yl, benzimidazol-2-yl and hydrogenated derivatives thereof.

OA is preferably methoxy, ethoxy, propoxy or butoxy, furthermore also pentyloxy or hexyloxy.

$R^1$ and $R^5$, independently of one another, are preferably H, A, CN, $NO_2$, Hal or —COA, where A is as defined above; in particular, $R^1$ and $R^5$ are H.

$R^2$ is preferably H or A, where A is as defined above; in particular H.

$R^3$ and $R^4$, independently of one another, are preferably H or —COA, in particular H.

X is preferably H, —C(=NH)—$NH_2$, —C(=N-methyl)-$NH_2$, 4-methylpyridin-2-yl, pyridin-2-yl, pyrimidin-2-yl, imidazol-2-yl, benzimidazol-2-yl and hydrogenated derivatives thereof.

Y is —$(CH_2)_m$- or

in particular —$(CH_2)_4$— or

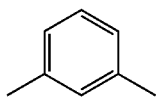

n and p, independently of one another, are preferably 1 or 2, in particular 1.

m is preferably 0, 2 or 4, in particular 0 or 4.

Preference is given to the compounds of the formulae IA and IB:

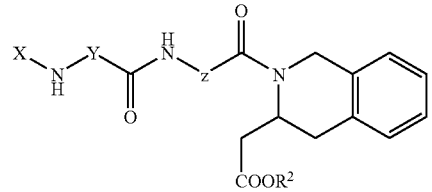

in which X, Y, Z and $R^2$ are as defined above. $R^2$ in the formulae IA and IB is, in particular, H Accordingly, the invention relates, in particular, to the compounds of the formula I in which at least one of the said radicals has one of the preferred meanings indicated above. Some preferred groups of compounds can be expressed by the following sub-formulae I1 to I36:

I1

I2

I3

I4
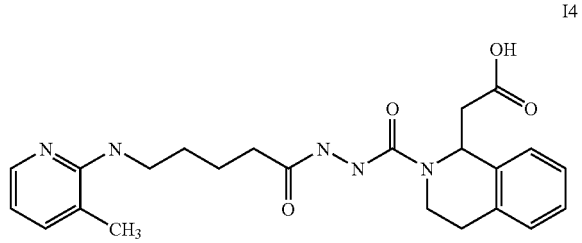
I5
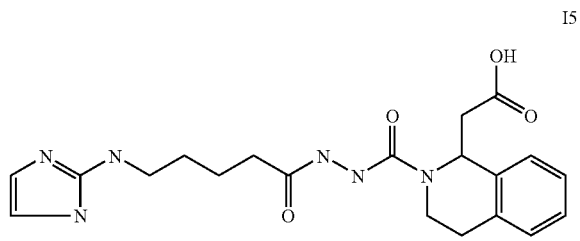
I6
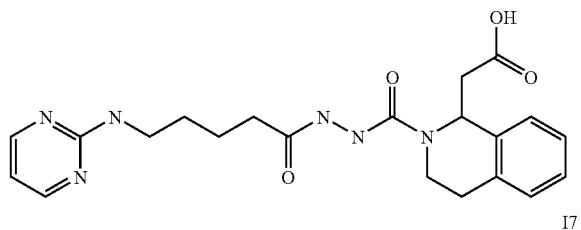
I7
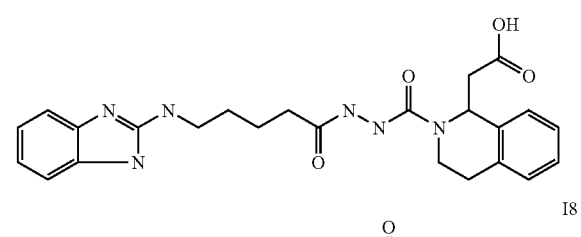
I8
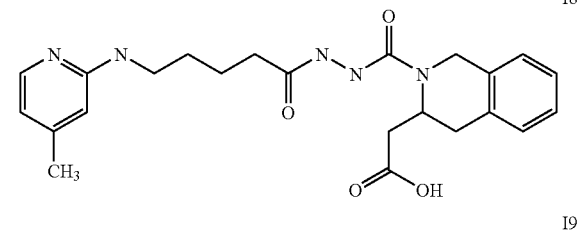
I9
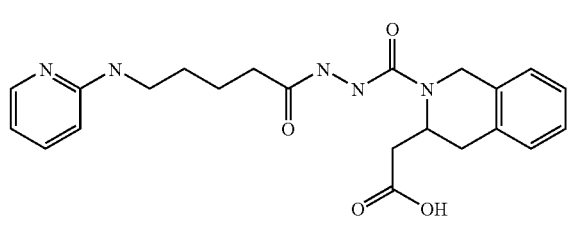
I10
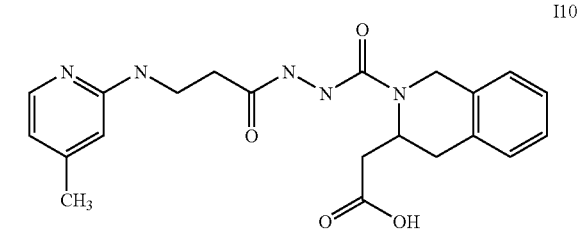
I11
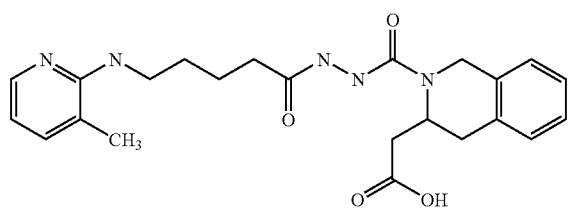
I12
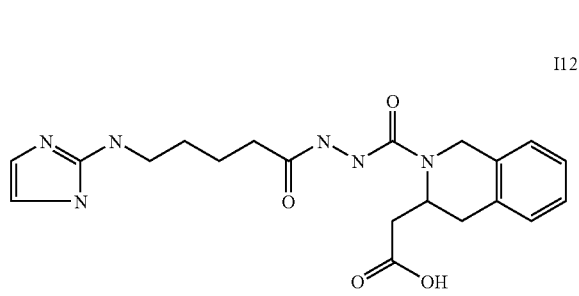
I13
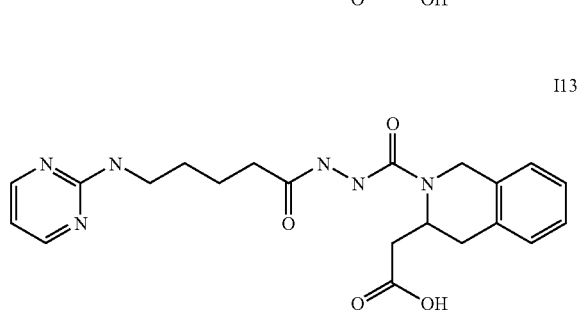
I14
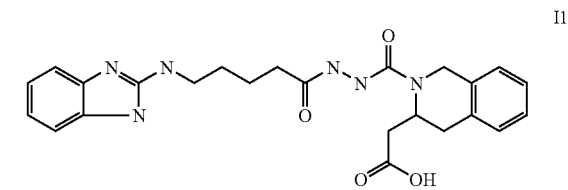
I15
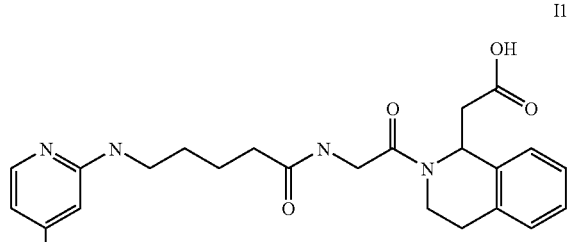
I16
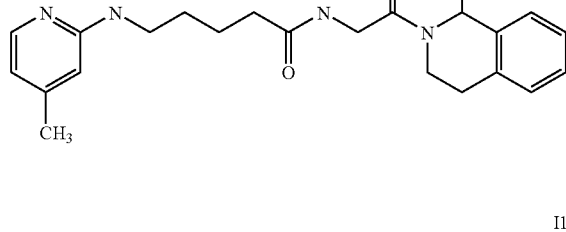
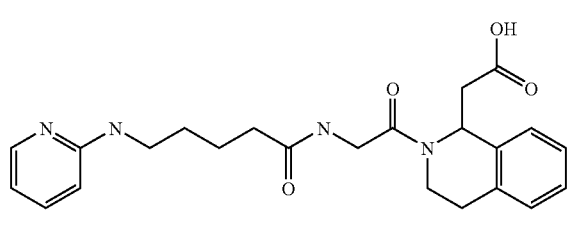

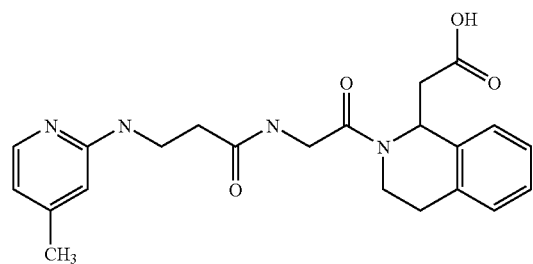
I17
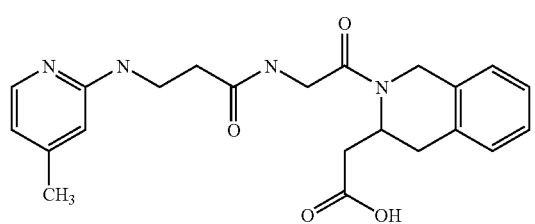
I24
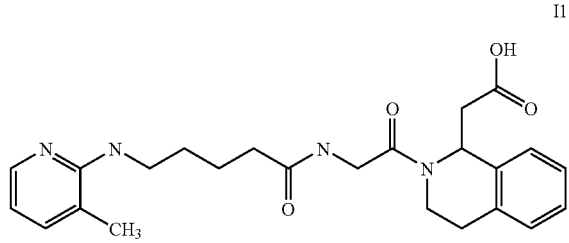
I18
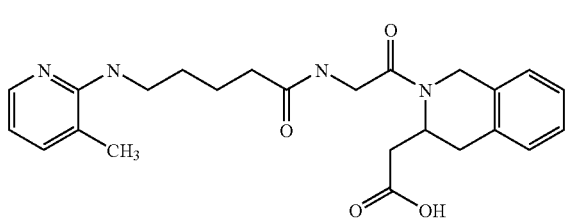
I25
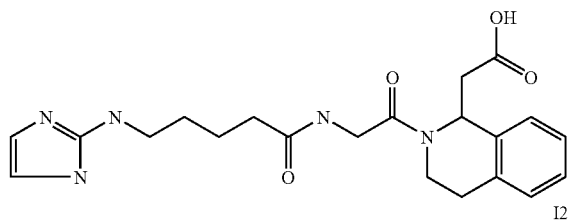
I19
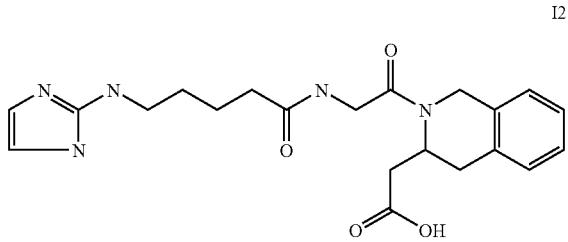
I26
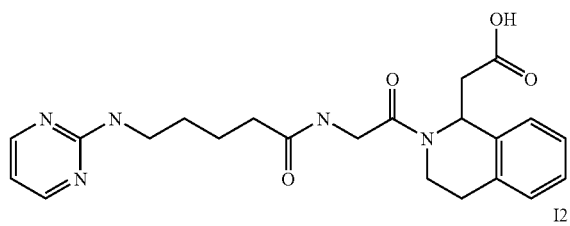
I20
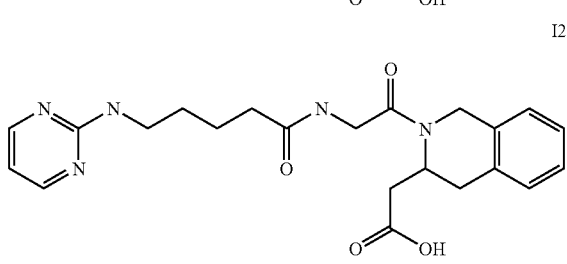
I27
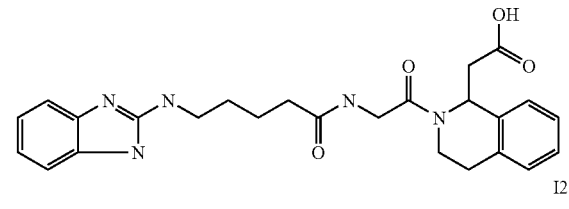
I21
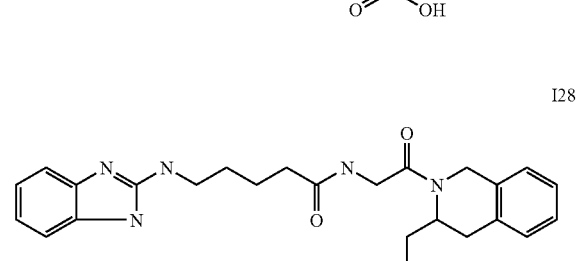
I28
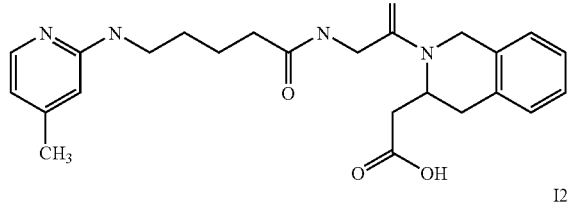
I22
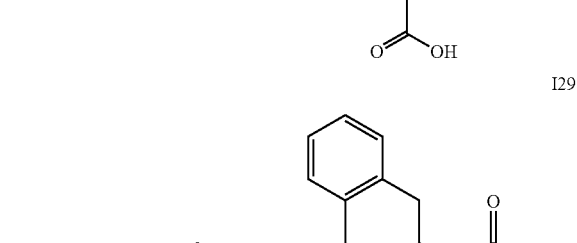
I29
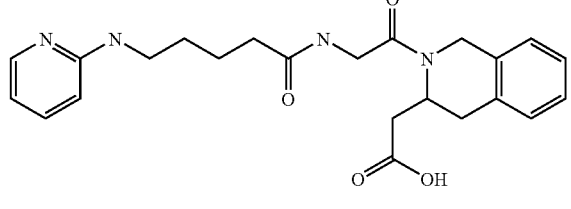
I23
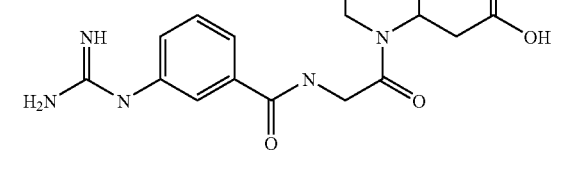

-continued

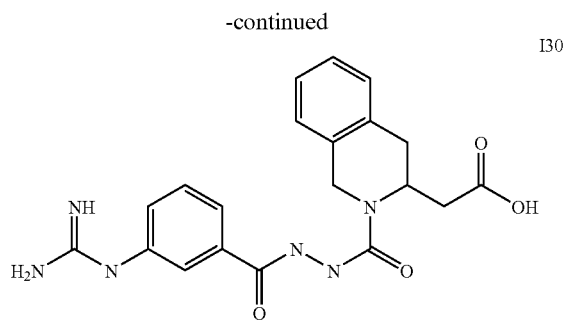
I30

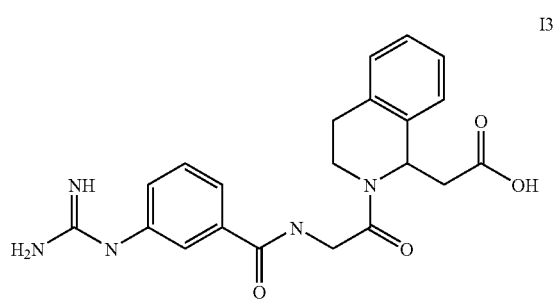
I31

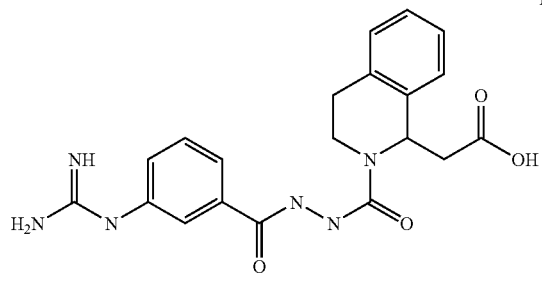
I32

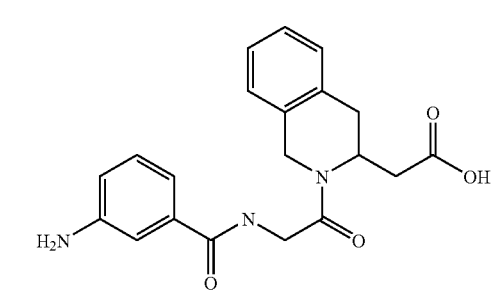
I33

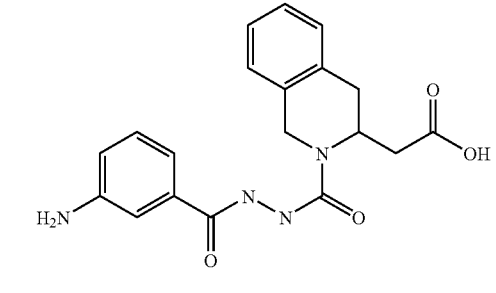
I34

-continued

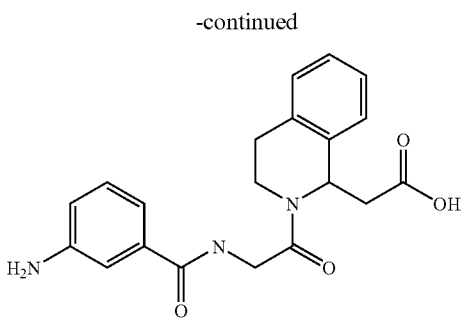
I35

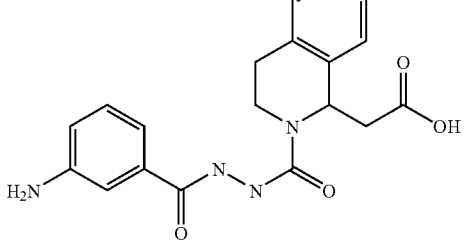
I36

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants which are known per se, but are not mentioned here in greater detail.

If desired, the starting materials can also be formed in situ, so that they are not isolated from the reaction mixture, but instead are immediately converted further into the compounds of the formula I.

Compounds of the formula I can preferably be obtained under the conditions of a peptide synthesis. Use is advantageously made here of conventional methods of peptide synthesis, as described, for example, in Houben-Weyl, l.c., Volume 15/II, pages 1 to 806 (1974).

The direct precursors of the compounds of the formula I can also be built up on a solid phase, for example a swellable polystyrene resin, as described, for example, by Merrifield (Angew. Chem. 97, 801–812, 1985). Solid phases which can be used are in principle all supports as are known, for example, from solid-phase peptide chemistry or nucleic acid synthesis. Suitable polymeric support materials are polymeric solid phases, preferably having hydrophilic properties, for example crosslinked polysugars, such as cellulose, sepharose or Sephadex[R], acrylamides, polyethylene glycol-based polymers or tentacle polymers[R].

The solid phase employed is preferably trityl chloride-polystyrene resin, 4-methoxytrityl chloride resin, Merrifield resin or Wang resin.

Thus, compounds of the formula I can be obtained by reacting a compound of the formula II with a compound of the formula III and subsequently removing the protecting groups or the solid phase.

The compounds of the formula I can likewise, be obtained by reacting a compound of the formula IV with a compound of the formula V and subsequently removing the protecting groups.

The coupling reaction preferably succeeds in the presence of a dehydrating agent, for example a carbodiimide, such as DCCI or EDCI, furthermore, for example, propanephosphonic anhydride (cf: Angew. Chem. 1980, 92, 129), diphenylphosphoryl azide or 2-ethoxy-N-ethoxycarbonyl-1,2-dihydroquinoline, in an inert solvent, for example a halogenated hydrocarbon, such as dichloromethane, an ether, such as tetrahydrofuran or dioxane, an amide, such as DMF or dimethylacetamide, a nitrile, such as acetonitrile, in dimethyl sulfoxide or in the presence of this solvent, at temperatures between about −10 and 40°, preferably between 0 and 30°. In order to promote intramolecular cyclisation ahead of intermolecular peptide binding, it is advantageous to work in dilute solutions. The reaction time, depending on the conditions used, is between a few minutes and 14 days.

Instead of compounds of the formulae II and/or IV, it is also possible to employ derivatives of compounds of the formulae II and/or IV, preferably a pre-activated carboxylic acid, or a carboxylic acid halide, a symmetrical or mixed anhydride or an active ester. Radicals of this type for activation of the carboxyl group in typical acylation reactions have been described in the literature (for example in the standard works, such as Houben-Weyl, Methoden der organischen Chemie [Methods of Organic Chemistry], Georg-Thieme-Verlag, Stuttgart). Activated esters are advantageously formed in situ, for example by addition of HOBt or N-hydroxysuccinimide.

The reaction is generally carried out in an inert solvent; if a carboxylic acid halide is used, it is carried out in the presence of an acid-binding agent, preferably an organic base, such as triethylamine, dimethylaniline, pyridine or quinoline.

The addition of an alkali or alkaline-earth metal hydroxide, carbonate or bicarbonate or another salt of a weak acid of the alkali or alkaline-earth metals, preferably of potassium, sodium, calcium or caesium, may also be favourable.

The compounds of the formula I can furthermore be obtained by liberating them from their functional derivatives by solvolysis, in particular hydrolysis, or by hydrogenolysis.

Preferred starting materials for the solvolysis or hydrogenolysis are those which otherwise conform to the formula I, but in which one or more free amino and/or hydroxyl groups have been replaced by corresponding protected amino and/or hydroxyl groups, in particular those in which an H—N group has been replaced by an $SG^1$—N group, in which $SG^1$ is an amino-protecting group, and/or those in which the H atom of a hydroxyl group has been replaced by a hydroxyl-protecting group, for example those which conform to the formula I, but in which a —COOH group has been replaced by a —COO$SG^2$ group, in which $SG^2$ is a hydroxyl-protecting group.

It is also possible for a plurality of—identical or different—protected amino and/or hydroxyl groups to be present in the molecule of the starting material. If the protecting groups present differ from one another, they can in many cases be removed selectively (cf. in this respect: T. W. Greene, P. G. M. Wuts, *Protective Groups in Organic Chemistry*, 2nd Edn., Wiley, New York 1991 or P. J. Kocienski, *Protecting Groups*, 1st Edn., Georg Thieme Verlag, Stuttgart-New York, 1994), H. Kunz, H. Waldmann in *Comprehensive Organic Synthesis*, Vol. 6 (Eds. B. M. Trost, I. Fleming, E. Winterfeldt), Pergamon, Oxford, 1991, pp. 631–701).

The term "amino protecting group" is generally known and relates to groups which are suitable for protecting (blocking) an amino group against chemical reactions. Typical of such groups are, in particular, unsubstituted or substituted acyl, aryl, aralkoxymethyl or aralkyl groups. Since the amino protecting groups are removed after the desired reaction (or synthesis sequence), their type and size is furthermore not crucial; however, preference is given to those having 1–20 carbon atoms. The term "acyl group" is to be understood in the broadest sense in connection with the present process. It includes acyl groups derived aliphatic, araliphatic, alicyclic, aromatic and heterocyclic carboxylic acids or sulfonic acids, as well as, in particular, alkoxycarbonyl, alkenyloxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as phenoxyacetyl; alkoxycarbonyl, such as methoxycarbonyl, ethoxycarbonyl, 2,2,2-trichloroethoxycarbonyl, Boc and 2-iodoethoxycarbonyl; alkenyloxycarbonyl, such as allyloxycarbonyl (Aloc), aralkoxycarbonyl, such as CBZ (synonymous with Z), 4-methoxybenzyloxycarbonyl (MOZ), 4-nitrobenzyloxycarbonyl and 9-fluorenylmethoxycarbonyl (Fmoc); 2-(phenylsulfonyl)ethoxycarbonyl; trimethylsilylethoxycarbonyl (Teoc), and arylsulfonyl, such as 4-methoxy-2,3,6-trimethylphenylsulfonyl (Mtr). Preferred amino protecting groups are Boc, Fmoc and Aloc, furthermore Z, benzyl and acetyl.

The term "hydroxyl protecting group" is likewise generally known and relates to groups which are suitable for protecting a hydroxyl group against chemical reactions. Typical of such groups are the above-mentioned unsubstituted or substituted aryl, aralkyl, aroyl or acyl groups, furthermore also alkyl groups, alkyl-, aryl- and aralkylsilyl groups, and O,O— and O,S-acetals. The nature and size of the hydroxyl protecting groups is not crucial since they are removed again after the desired chemical reaction or synthesis sequence; preference is given to groups having 1–20 carbon atoms, in particular 1–10 carbon atoms. Examples of hydroxyl protecting groups are, inter alia, aralkyl groups, such as benzyl, 4-methoxybenzyl and 2,4-dimethoxybenzyl, aroyl groups, such as benzoyl and p-nitrobenzoyl, acyl groups, such as acetyl and pivaloyl, p-toluenesulfonyl, alkyl groups, such as methyl and tert-butyl, but also allyl, alkylsilyl groups, such as trimethylsilyl (TMS), triisopropylsilyl (TIPS), tert-butyldimethylsilyl (TBS) and triethylsilyl, trimethylsilylethyl, aralkylsilyl groups, such as tert-butyldiphenylsilyl (TBDPS), cyclic acetals, such as isopropylidene acetal, cyclopentylidene acetal, cyclohexylidene acetal, benzylidene acetal, p-methoxybenzylidene acetal and o,p-dimethoxybenzylidene acetal, acyclic acetals, such as tetrahydropyranyl (Thp), methoxymethyl (MOM), methoxyethoxymethyl (MEM), benzyloxymethyl (BOM) and methylthiomethyl (MTM). Particularly preferred hydroxyl protecting groups are benzyl, acetyl, tert-butyl and TBS.

The liberation of the compounds of the formula I from their functional derivatives is known from the literature for the protecting group used in each case (for example T. W. Greene, P. G. M. Wuts, *Protective Groups in Organic Chemistry*, 2nd Edn., Wiley, New York 1991 or P. J. Kocienski, *Protecting Groups*, 1st Edn., Georg Thieme Verlag, Stuttgart-New York, 1994). Use may also be made here of variants which are known per se, but are not mentioned here in greater detail.

A base of the formula I can be converted into the associated acid-addition salt using an acid, for example by reaction of equivalent amounts of the base and the acid in an inert solvent, such as ethanol, followed by evaporation. Suitable acids for this reaction are, in particular, those which give physiologically acceptable salts. Thus, it is possible to use inorganic acids, for example sulfuric acid, sulfurous acid, dithionic acid, nitric acid, hydrohalic acids, such as hydrochloric acid or hydrobromic acid, phosphoric acids, such as, for example, orthophosphoric acid, sulfamic-acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, hexanoic acid, octanoic acid, decanoic acid, hexadecanoic acid, octadecanoic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, benzenesulfonic acid, trimethoxybenzoic acid, adamantanecarboxylic acid, p-toluenesulfonic acid, glycolic acid, embonic acid, chlorophenoxy-acetic acid, aspartic acid, glutamic acid, proline, glyoxylic acid, palmitic acid, para-chlorophenoxyisobutyric acid, cyclohexanecarboxylic acid, glucose 1-phosphate, naphthalenemono- and -disulfonic acids or laurylsulfuric acid. Salts with physiologically unacceptable acids, for example picrates, can be used to isolate and/or purify the compounds of the formula I. On the other hand, compounds of the formula I can be converted into the corresponding metal salts, in particular alkali metal salts or alkaline earth metal salts, or into the corresponding ammonium salts, using bases (for example sodium hydroxide, potassium hydroxide, sodium carbonate or potassium carbonate). Suitable salts are furthermore substituted ammonium salts, for example the dimethyl-, diethyl- or diisopropyl-ammonium salts, monoethanol-, diethanol- or diisopropylammonium salts, cyclohexyl- or dicyclohexylammonium salts, dibenzylethylenediammonium salts, furthermore, for example, salts with arginine or lysine The invention furthermore relates to the use of the compounds of the formula I and/or physiologically acceptable salts thereof for the preparation of a medicament.

The invention furthermore relates to pharmaceutical preparations comprising at least one compound of the formula I and/or one of its physiologically acceptable salts or solvates thereof which are prepared, in particular, by non-chemical methods. In this case, the compounds of the formula I can be brought into a suitable dosage form here together with at least one solid, liquid and/or semi-liquid excipient or adjuvant and, if desired, in combination with one or more further active ingredients.

These preparations can be used as medicaments in human or veterinary medicine. Suitable excipients are organic or inorganic substances which are suitable for enteral (for example oral), parenteral or topical administration and do not react with the novel compounds, for example water, vegetable oils, benzyl alcohols, alkylene glycols, polyethylene glycols, glycerol triacetate, gelatine, carbohydrates, such as lactose or starch, magnesium stearate, talc or vaseline. Suitable for oral administration are, in particular, tablets, pills, coated tablets, capsules, powders, granules, syrups, juices or drops, suitable for rectal administration are suppositories, suitable for parenteral administration are solutions, preferably oily or aqueous solutions, furthermore suspensions, emulsions or implants, and suitable for topical application are ointments, creams or powders. The novel compounds can also be lyophilised and the resultant lyophilisates used, for example, for the preparation of injection preparations. The preparations indicated may be sterilised and/or comprise assistants, such as lubricants, preservatives, stabilisers and/or wetting agents, emulsifiers, salts for modifying the osmotic pressure, buffer substances, dyes, flavours and/or a plurality of further active ingredients, for example one or more vitamins. For administration as an inhalation spray, it is possible to use sprays in which the active ingredient is either dissolved or suspended in a propellant gas or propellant gas mixture (for example $CO_2$ or chlorofluorocarbons). The active ingredient is advantageously used here in micronised form, in which case one or more additional physiologically acceptable solvents may be present, for example ethanol. Inhalation solutions can be administered with the aid of conventional inhalers.

The compounds of the formula I and physiologically acceptable salts thereof can be used as integrin inhibitors in the combating of diseases, in particular thromboses, cardiac infarction, coronary heart diseases, arteriosclerosis, tumours, osteoporosis, inflammation and infections.

The compounds of the formula I and physiologically acceptable salts thereof can also be used in the case of pathological processes maintained or propagated by angiogenesis, in particular in the case of tumours or rheumatoid arthritis.

The substances according to the invention are generally administered analogously to other known, commercially available peptides, but in particular analogously to the compounds described in U.S. Pat. No. 4,472,305, preferably in doses of from about 0.05 to 500 mg, in particular from 0.5 to 100 mg, per dosage unit. The daily dose is preferably from about 0.01 to 2 mg/kg of body weight. However, the specific dose for each patient depends on a wide variety of factors, for example on the efficacy of the specific compound employed, on the age, body weight, general state of health, sex, on the diet, on the time and method of administration, on the rate of excretion, medicament combination and severity of the particular disease to which the therapy applies. Parenteral administration is preferred.

Furthermore, the compounds of the formula I can be used as integrin ligands for the production of columns for affinity chromatography for the purification of integrins.

In this method, the ligand, i.e. a compound of the formula I, is covalently coupled to a polymeric support via an anchor function, for example the carboxyl group of Asp.

The materials for affinity chromatography for integrin purification are prepared under conditions as are usual and known per se for the condensation of amino acids.

The compounds of the formula I have one or more centres of chirality and can therefore exist in racemic or optically active form. Racemates obtained can be resolved into the enantiomers mechanically or chemically by methods known per se. Diastereomers are preferably formed from the racemic mixture by reaction with an optically active resolving agent. Examples of suitable resolving agents are optically active acids, such as the D and L forms of tartaric acid, diacetyltartaric acid, dibenzoyltartaric acid, mandelic acid, malic acid, lactic acid, and the various optically active camphorsulfonic acids, such as β-camphorsulfonic acid. Resolution of the enantiomers with the aid of a column filled with an optically active resolving agent (for example dinitrobenzoylphenylglycine) is also advantageous; an example of a suitable eluent is a mixture of hexane/isopropanol/acetonitrile, for example in the volume ratio 82:15:3.

It is of course also possible to obtain optically active compounds of the formula I by the methods described above by using starting materials which are already optically active.

Above and below, all temperatures are given in ° C. In the following examples, "conventional work-up" means that, if necessary, water is added, if necessary, depending on the constitution of the end product, the pH is adjusted to a value between 2 and 10, the mixture is extracted with ethyl acetate or dichloromethane, the phases are separated, the organic phase is dried over sodium sulfate and evaporated, and the product is purified by chromatography on silica gel and/or by crystallisation.

RT=retention time (minutes) in HPLC in the following systems:
Columns from Omnicrom YMC:
1. 4.6×250 mm, 5 µm, $C_{18}$ (analysis);
2. 30×250 mm, 7 µm, $C_{18}$ (preparation).

The eluents used are gradients comprising acetonitrile (B) with 0.1% of TFA and water (A) with 0.1% of TFA (data in each case in per cent by volume of acetonitrile). The retention time RT was determined at a flow rate of 1 ml/min.

Detection at 220 nm.

The diastereomers are preferably separated under the stated conditions.

Mass spectrometry (MS): ESI (electrospray ionisation) $(M+H)^+$.

FAB (fast atom bombardment) $(M+H)^+$.

1. Material and General Working Procedures

Solvents for the synthesis were either obtained in "technical grade" and distilled before use or purchased from Fluka (Seelze) or Merck (Darmstadt) in purity grades "absolute" or "for synthesis". NMP (distilled) was obtained free of charge from BASF (Ludwigshafen). Solvents for column chromatography were obtained in "technical grade" and either distilled before use or employed without distillation (hexane). The HPLC solvents acetonitrile (solvent B) and TFA were purchased in purity grade "gradient grade" from Merck (Darmstadt), water (solvent A) was deionised and treated with a Milli-Q system from Millipore (Molsheim, France).

Fmoc-protected amino acids were purchased from Novabiochem, Advanced ChemTech, MultiSynTech or PepTech Corporation (Cambridge, USA).

For manual solid-phase synthesis, use was made of PE syringes from Becton-Dickinson (Fraga, Spain) or Braun (Melsungen) with PE frits from Roland Vetter Laborbedarf (Ammerbuch). In order to mix the resin suspension, the syringes were rotated at about 30 rpm. The resin was charged in glass shaking vessels.

Air- or moisture-sensitive reactions were carried out in dry glass vessels and under an argon atmosphere (99.996%). Hygroscopic solvents and/or solvents which had been rendered absolute were transferred into syringes under argon.

For the HPLC purification, the compounds were dissolved in DMSO, acetonitrile or methanol ("gradient grade") and filtered through an RC 15 or RC 25 (RC membrane, 0.45 µm) syringe filter from Sartorius (Göttingen). Analytical, semi-preparative and preparative separations were carried out in two HPLC systems from Amersham Pharmacia Biotech (analytical: Äkta Basic 10F with A-900 autosampler; preparative: Äkta Basic 100F with P-900 pump system and UV-900 detector) and two systems from Beckman (Gold system with 125 solvent module and 166 detector module; 110B pump system, 420 control unit and Knauer Uvicord detector). The following columns were used for analytical separations: ODS-A $C_{18}$ (250 mm×4.6 mm, 5 µm, flow rate: 1 ml/min) from Omnicrom YMC; for semi-preparative separations: ODS-A $C_{18}$ (250 mm×20 mm, 5 µm or 10 µm, flow rate: 8 ml/min) from Omnicrom YMC; for preparative separations: ODS-A $C_{18}$ (250 mm×30 mm, 10 µm, flow rate: 25 ml/min) from Omnicrom YMC and Nucleosil $C_{18}$ (250 mm×20 mm, 7 µm, flow rate: 25 ml/min) from Macherey-Nagel. The compounds were eluted with linear gradients (30 min) of acetonitrile (solvent B) in water (solvent A) and 0.1% (v/v) of TFA. For analytical purity determination of the compounds after semi-preparative or preparative HPLC purification, the peak integral of the analytical HPLC chromatogram was evaluated at a detector wavelength of 220 nm.

The column chromatography was carried out using silica gel 60 (230–400 mesh ASTM, particle size 0.040–0.063 mm) from Merck (Darmstadt), flash chromatography was carried out at a pressure of 1–1.2 bar above atmospheric.

Thin-layer chromatography (TLC) and the determination of the $R_f$ values were carried out using aluminium TLC plates coated with silica gel 60 $F_{254}$ from Merck (Darmstadt). For detection, the TLC plates were viewed under UV light ($\lambda$=254 nm).

Melting points were determined by the Dr Tottoli method in a Büchi 510 melting point apparatus and are uncorrected.

All $^1$H-NMR and $^{13}$C-NMR spectra were recorded on a Bruker AC250 or DMX500 spectrometer at 300 K, the spectral data were processed on Bruker Aspekt 1000 (AC 250) or on Silicon Graphics Indy, O2 and Octane workstations with XWINNMR software. Chemical shifts ($\delta$) are given in parts per million (ppm) relative to tetramethylsilane, and coupling constants are given in hertz (Hz). The internal standard used was tetramethylsilane or the solvent peak: DMSO-$d_6$: 2.49 ppm ($^1$H-NMR) and 39.5 ppm ($^{13}$C-NMR); CDCl$_3$: 7.24 ppm ($^1$H-NMR) and 77.0 ppm ($^{13}$C-NMR). $^{13}$C-NMR spectra were recorded with $^1$H broadband decoupling. The signal assignment was in most cases carried out with the aid of HMQC and COSY experiments.

Mass spectra were recorded by the electron impact (EI) and chemical ionisation (CI) techniques on a Finnigan MAT 8200 instrument. Electrospray ionisation (ESI) mass spectra were recorded on a Finnigan LCQ mass spectrometer in combination with a Hewlett Packard 1100 HPLC system with an ODS-A $C_{18}$ (125 mm×2 mm, 3 µm, flow rate: 0.2 ml/min) column from Omnicrom YMC. The compounds were eluted with a linear gradient (15 min) of acetonitrile (solvent B) in water (solvent A) and 0.1% (v/v) of formic acid. Mass spectra are given in the form "X (Y) [M+Z]$^{+}$", where "X" is the detected mass, "Y" is the observed intensity of the mass peak, "M" is the molecule investigated, and "Z" is the adducted cation.

High-resolution mass spectra (HRMS) were recorded by Koka Jajasimhulu Ph.D. (University of Cincinnati, USA) using the electrospray ionisation-time of flight (ESI-TOF) technique.

Lyophilisation was carried out using the Alpha 2–4 instrument from Christ (Osterode).

AAV1: Loading of TCP Resin

The corresponding Fmoc-protected amino acid (1.56 mmol, 1.5 eq) and DIPEA (177 µl, 1.03 mmol) are added to pre-swollen TCP resin (1.16 g, maximum loading: 0.9 mmol/g) in dry CH$_2$Cl$_2$ (6 ml, 10 min). After 5 minutes, further DIPEA (91 µl, 0.52 mmol) is added, and the resin is shaken. After 2 hours, methanol (1.16 ml) is added in order to cap the unreacted trityl groups, and the resin is shaken for a further 15 minutes. The resin is then washed with dry CH$_2$Cl$_2$ (5×20 ml, 3 minutes each time), NMP (5×20 ml, 3 minutes each time) and again with dry CH$_2$Cl$_2$ (5×20 ml, 3 minutes each time) and finally with a mixture-of methanol/

$CH_2Cl_2$ (1:1, 20 ml) and methanol (20 ml). The resin is dried in a high vacuum, and the loading can be determined using the following equation:

$$l = \frac{(m_2 - m_1) \times 1000}{(MW - 36.45) \times m_2}$$

l loading of the resin with unit [mmol/g]
$m_1$ weight of the resin before coupling [g]
$m_2$ weight of the dried resin after coupling [g]
MW molecular weight of the Fmoc-protected amino acid/carboxylic acid unit [g/mol]

The error arising through the difference masses of Cl and MeO can be neglected.

AAV 2: Removal of the Fmoc Protecting Group

The resin (100 mg) is pre-swollen in NMP (5 ml, 10 min). The Fmoc protecting group is removed by treatment with a freshly prepared 20% piperidine solution (v/v) in NMP (5 ml) for 15 minutes. The resin is then washed with NMP (5×5 ml, 3 minutes each time), and a 20% piperidine solution (v/v) in NMP (5 ml, 15 minutes) is again added. Finally, the resin is washed with NMP (5×5 ml, 3 minutes each time).

AAV 3: Coupling of 5-(9H-fluoren-9-ylmethoxy)-3H-1,3,4-oxadiazol-2-one (142) to Resin-Bound, Free Amines by the Gibson Method In order to deprotect the resin-bound amine, 20% piperidine (v/v) in NMP (2×5 ml, 15 minutes each time) is added to the TCP resin (100 mg, 0.354 mmol/g, 0.035 mmol). The resin is then washed with NMP (5×5 ml, 3 minutes each time) and dry $CH_2Cl_2$ (5×5 ml, 3 minutes each time) and then swollen in dry $CH_2Cl_2$ (5 ml) for half an hour. A solution of 5-(9H-fluoren-9-ylmethoxy)-3H-1,3,4-oxadiazol-2-one (142) (30.5 mg, 0.108 mmol, 3.1 eq) in dry $CH_2Cl_2$ (1 ml) is then added to the resin, and the mixture is shaken for 90 minutes. The reaction is terminated by washing with $CH_2Cl_2$ (5×5 ml, 3 minutes each time) and NMP (5×5 ml, 3 minutes each time).

AAV 4: Coupling with HATU/HOAt

The resin-bound, free amine or hydrazine (0.389 mmol) is washed with NMP (5×5 ml, 3-minutes each time). A solution of the suitable Fmoc-protected amino acid or of a carboxylic acid unit (0.779 mmol, 2 eq), HATU (296 mg, 0.779 mmol, 2 eq) and HOAt (106 mg, 0.779 mmol, 2 eq) in NMP (5 ml) is then added to the resin. Finally, sym-collidine (1027 µl, 7.79 mmol, 20 eq) is added, and the resin is shaken overnight. The resin is then washed with NMP (5×5 ml, 3 minutes each time), and the coupling step is repeated with the same reagents, amounts and reaction time. The resin is subsequently washed with NMP (5×5 ml, 3 minutes each time).

AAV 5: Removal from the TCP Resin

The compound is removed from the TCP resin in accordance with the following flow chart:

| Step | Reagents | Operation | Number | Time [min] |
|---|---|---|---|---|
| 1 | $CH_2Cl_2$ | washing | 3 | 10 |
| 2 | TFA/TIPS/$H_2O$ (18:1:1) | removal/deprotection | 3 | 30 |
| 3 | $CH_2Cl_2$ | washing | 3 | 3 |

For 100 mg of resin, 2 ml of removal solution were usually used. The combined filtrates from steps 2 and 3 were evaporated.

2. EXAMPLES

Example 1a)

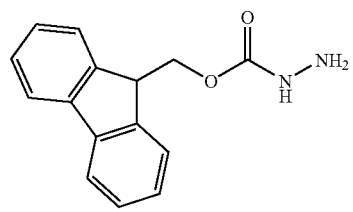

141

N-[(9H-Fluoren-9-ylmethoxy)carbonyl]hydrazine (141)

Boc-hydrazine (10.0 g, 75.6 mmol) and DIPEA (12.95 ml, 75.6 mmol) were dissolved in dry $CH_2Cl_2$ (200 ml) and cooled to 0° C. FmocCl (19.6 g, 75.8 mmol), dissolved in dry $CH_2Cl_2$ (100 ml), was then added over the course of 30 minutes, and the mixture was stirred overnight at room temperature. The organic phase was extracted with water (200 ml) and evaporated to a volume of about 100 ml. Trifluoroacetic acid (100 ml) was then carefully added at 0° C., and the mixture was stirred for 1.5 hours. The product was precipitated by careful addition of saturated $Na_2CO_3$ solution (300 ml) and dried, giving a colourless solid (18.02 g, 70.8 mmol, 94%).

m.p. 150–153° C.; $^1$H-NMR (250 MHz, DMSO-$d_6$, 300 K) δ=10.10 (bs, 1H, NH), 9.60 (bs, 1H, NH), 7.89 (d, J=7.6 Hz, 2H, arom), 7.70 (d, J=7.3 Hz, 2H, arom), 7.30–7.45 (m, 4H, arom), 4.48 (d, J=6.6 Hz, 2H, CO—$CH_2$), 4.27 (t, J=6.7 Hz, 1H, CO—$CH_2$—CH); $^{13}$C-NMR (62.9 MHz, DMSO-$d_6$, 300 K) δ=156.26, 143.59, 140.98, 127.96, 127.34, 125.33, 120.39, 67.00, 46.60; HRMS (ESI-TOF) for $C_{15}H_{15}N_2O_2$ [M+H]$^+$: 255.1134 (calc. 255.1119); analytical HPLC (5–90% in 30 min) $t_R$=16.47 min.

Example 1b)

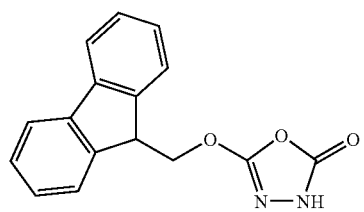

142

5-(9H-Fluoren-9-ylmethoxy)-3H-1,3,4-oxadiazol-2-one (142)

A suspension of N-[(9H-fluoren-9-ylmethoxy)carbonyl] hydrazine (141) (1.49 g, 5.78 mmol), CH$_2$Cl$_2$ (60 ml) and saturated NaHCO$_3$ solution (60 ml) was stirred vigorously at 0° C. for 5 minutes, and the solution was then left for 5 minutes without stirring. Phosgene (1.89 M in toluene, 7.95 ml, 15.0 mmol) was then carefully added to the lower, organic phase using a syringe, and stirring of the reaction mixture was begun again immediately after the addition. After 10 minutes, water (20 ml) and CH$_2$Cl$_2$ (20 ml) were added to the reaction mixture. The phases were then separated rapidly, the aqueous phase was extracted with CH$_2$Cl$_2$ (50 ml), and the combined organic phases were dried over Na$_2$SO$_4$. Removal of the solvent under reduced pressure and drying gave a colourless solid (1.35 g, 4.82 mmol, 83%).

m.p. 125° C.; $^1$H-NMR (250 MHz, CDCl$_3$, 300 K) δ=8.72 (bs, 1H, NH), 7.77 (d, J=7.5 Hz, 2H, arom), 7.59 (d, J=7.4 Hz, 2H, arom), 7.28–7.45 (m, 4H, arom), 4.49 (d, J=7.8 Hz, 2H, CH$_2$—CH), 4.32–4.41 (m, 1H, CH$_2$—CH).

Example 2a)

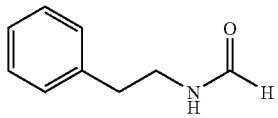

146

N-Phenylethylformamide (146)

A mixture of phenylethylamine (20.0 g, 0.165 mol) and formic acid (49.4 ml, 1.309 mol) was slowly heated to 200° C. Excess water and formic acid were distilled off in the process. The mixture was then kept at 200° C. for 1 hour, and the product was distilled under reduced pressure, giving a colourless oil (22.0 g, 0.147 mol, 89%).

$^1$H-NMR (250 MHz, DMSO-d$_6$, 300 K) δ=8.06 (bs, 1H, CHO), 7.16–7.32 (m, 5H, arom), 3.32–3.42 (m, 2H, NH—CH$_2$), 2.77 (t, J=7.2 Hz, 2H, NH—CH$_2$—CH$_2$); analytical HPLC (5–90% in 30 min) t$_R$=15.04 min.

Example 2b)

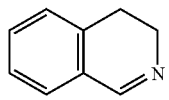

147

3,4-Dihydroisoquinoline (147)

Polyphosphoric acid (25 g) and phosphorus pentoxide (5.4 g, 38.0 mmol) were heated to 180° C. over the course of one hour in an oil bath under an argon atmosphere. N-Phenylethylformamide (146) (4.3 g, 28.8 mmol) was then added at 160° C., and the mixture was stirred for 1.5 hours at constant temperature. The mixture was then allowed to cool to room temperature, and water (40 ml) was added. The mixture was subsequently adjusted to pH 10 by careful addition of saturated aqueous NaOH solution. The mixture was then extracted with ether (500 ml), and the organic phase was separated off and dried using NaOH. Evaporation gave a brown oil (2.81 g, 21.4 mmol, 74%).

$^1$H-NMR (250 MHz, DMSO-d$_6$, 300 K) δ=8.32 (t, J=2.3 Hz, 1H, N—CH), 7.16–7.40 (m, 4H, arom), 3.59–3.66 (m, 2H, N—CH$_2$), 2.66 (t, J=7.3 Hz, 2H, N—CH$_2$—CH$_2$); analytical HPLC (5–90% in 30 min) t$_R$=8.29 min.

Example 2c)

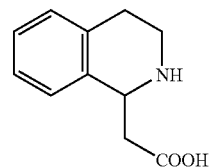

148

2-(1,2,3,4-Tetrahydro-1-isoquinolinyl)acetic acid (148)

3,4-Dihydroisoquinoline (147) (2.2 g, 16.77 mmol) and malonic acid (1.94 g, 16.77 mmol) were mixed at room temperature and heated at 120° C. for 1 hour in an oil bath. The mixture was then allowed to cool to room temperature, and the product was recrystallised from methanol (150 ml). Drying gave a colourless solid (1.52 g, 7.99 mmol, 48%).

m.p. 230° C. decomp; $^1$H-NMR (250 MHz, D$_2$O, 300 K) δ=7.13–7.23 (m, 4H, arom), 4.65 (t, J=6.9 Hz, 1H, CH—NH), 3.44–3.54 (m, 1H, NH—CH$_2$), 3.24–3.34 (m, 1H, NH—CH$_2$), 2.95–3.03 (m, 2H, NH—CH$_2$—CH$_2$), 2.79 (d, J=6.1 Hz, 2H, CH$_2$—COOH); HRMS (ESI-TOF) for C$_{11}$H$_{14}$NO$_2$ [M+H]$^+$: 192.1047 (calc. 192.1025); analytical HPLC (5–90% in 30 min) t$_R$=10.15 min.

Example 2d)

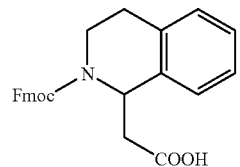

149

9H-Fluoren-9-ylmethyl 1-carboxymethyl-3,4-dihydro-1H-isoquinoline-2-carboxylate (149)

A suspension of 2-(1,2,3,4-tetrahydro-1-isoquinolinyl) acetic acid (148) (0.9 g, 4.73 mmol), saturated NaHCO$_3$ solution (15 ml) and dioxane (5 ml) was cooled to 0° C. FmocCl (1.35 g, 5.2 mmol), dissolved in dioxane (5 ml), was then added dropwise over the course of 30 minutes, and the mixture was stirred overnight. The mixture was then washed by shaking with ether (30 ml), and the aqueous phase was adjusted to pH 1 using conc. HCl. The product was then extracted with ethyl acetate (50 ml), and the organic phase was dried over MgSO$_4$ and evaporated. The crude product was subsequently purified by column chromatography (ethyl acetate/hexane/acetic acid, 1:1:1%) and dried, giving a colourless foam (1.54 g, 3.73 mmol, 79%).

m.p. 61–63° C.; TLC $R_f$ (ethyl acetate/hexane/acetic acid, 1:1:1%)=0.54; $^1$H-NMR (250 MHz, DMSO-$d_6$, 300 K) δ=7.79–7.91 (m, 2H, arom), 7.63–7.66 (m, 2H, arom), 7.05–7.39 (m, 8H, arom), 5.40–5.52 (m, 1H, NH—CH), 4.37–4.42 (m, 1H, COO—CH$_2$—CH), 4.25–4.32 (m, 2H, COO—CH$_2$), 3.62–4.02 (m, 1H, N—CH$_2$), 3.27–3.38 (m, 1H, N—CH$_2$), 2.52–2.76 (m, 4H, N—CH—CH$_2$ and N—CH$_2$—CH$_2$); MS (ESI) m/e 179.1 (30), 414.0 (20) [M+H]$^+$, 436.2 (25) [M+Na]$^+$, 492.8 (15), 826.7 (5) [2M+H]$^+$, 849.1 (45) [2M+Na]$^+$, 865.1 (100) [2M+K]$^+$; HRMS (ESI-TOF) for $C_{26}H_{24}NO_4$ [M+H]$^+$: 414.1721 (calc. 414.1705); analytical HPLC (5–90% in 30 min) $t_R$=27.53 min.

Example 3a)

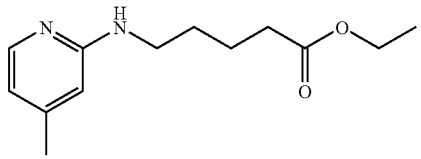

Ethyl 5-[N-(4-methylpyridin-2-yl)amino]pentanoate

Ethyl 5-bromopentanoate (33.03 g, 25 ml, 158 mmol) and 2-amino-4-methylpyridine (32.9 g, 304 mmol) were refluxed overnight at 130° C. (oil-bath temperature). After cooling to room temperature, saturated NaHCO$_3$ solution (100 ml) was added to the reaction mixture, which was then extracted with ether (5×100 ml). The combined organic phases were dried over MgSO$_4$, and the solvent was removed. The crude product was purified by flash chromatography (ethyl acetate/hexane, 1:1, 2 l; 3:2, 1 l; 7:3, 1 l; 4:1, 1 l), and dried, giving a colourless solid (16.7 g, 70.7 mmol, 45%).

m.p. 41–43° C.; TLC $R_f$ (ethyl acetate/hexane, 1:1)=0.26.; $^1$H-NMR (250 MHz, DMSO-$d_6$, 300 K) δ=7.90 (d, J=5.3 Hz,1H, N—CH—CH), 6.38 (d, J=5.2 Hz, 1H, N—C—CH), 6.17 (s, 1H, N—CH—CH), 4.51 (bs, 1H, NH), 4.11 (q, J=7.2 Hz, 2H, O—CH$_2$—CH$_3$), 3.25 (q, J=6.3 Hz, 2H, NH—CH$_2$), 2.33 (t, J=7.0 Hz, 2H, CH$_2$—CO), 2.21 (s, 3H, C—CH$_3$),1.60–1.80 (m, 4H, NH—CH$_2$—CH$_2$—CH$_2$), 1.23 (t, J=7.0 Hz, 2H, O—CH$_2$—CH$_3$); analytical HPLC (5–90% in 30 min) $t_R$=13.58 min.

Example 3b)

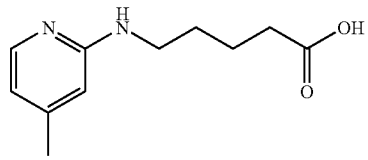

5-[N-(4-Methylpyridin-2-yl)amino]pentanoic acid

Ethyl 5-[N-(4-methylpyridin-2-yl)amino]pentanoate (16.7 g, 70.7 mmol, obtainable in accordance with Example 3a)) was dissolved in methanol (20 ml), 2N aqueous NaOH (71 ml, 141 mmol) was added, and the mixture was stirred overnight at room temperature. The solvent was then removed, and the resultant solid was extracted thoroughly with CHCl$_3$ (500 ml) and an excess of DIPEA. The filtrate was evaporated and dried, giving a colourless solid (3.92 g, 18.8 mmol, 27%).

m.p. 138–140° C; $^1$H-NMR (250 MHz, DMSO-$d_6$, 300 K) δ=7.79 (d, J=5.2 Hz, 1H, NH), 6.26–6.30 (m, 2H, arom. $C^5$—H and $C^6$—H), 6.22 (s, 1H, arom. $C^3$—H), 3.17 (dt, J=5.8 Hz, 2H, NH—CH$_2$), 2.21 (t, J=7.0 Hz, 2H, CH$_2$—CH$_2$—CO), 2.11 (s, 3H, $C^{quat.}$—CH$_3$), 1.41–1.58 (m, 4H, CH$_2$—CH$_2$—CH$_2$—CH$_2$); $^{13}$C-NMR (67.5 MHz, DMSO-$d_6$, 300 K) δ=174.6 (COOH), 159.3, 147.3, 146.8, 113.1, 107.9, 40.5, 33.7, 28.8, 22.4, 20.8; HRMS (ESI-TOF) for $C_{11}H_{17}N_2O_2$ [M+H]$^+$: 209.1293 (calc. 209.1290); analytical HPLC (5–90% in 30 min) $t_R$=9.83 min.

Example 4

WDCE10

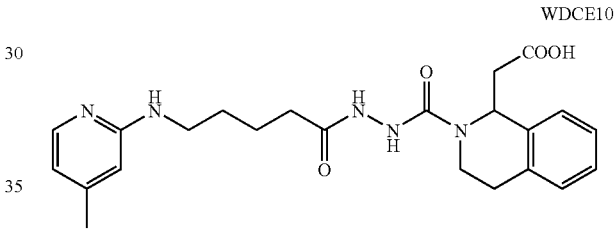

TCP resin was loaded with 9H-fluoren-9-ylmethyl 1-carboxymethyl-3,4-dihydro-1H-isoquinoline-2-carboxylate (149 from Example 2d)) (0.48 g, 1.16 mmol) as described in AAV 1 ($m_1$=0.84 g, $m_2$=1.0 g, l=0.426 mmol/g). Fmoc deprotection and coupling of the freshly prepared 5-(9H-fluoren-9-ylmethoxy)-3H-1,3,4-oxadiazol-2-one (142 from Example 1b)) (385 mg, 1.32 mmol) were carried out as described in AAV 2 and 3, coupling of 5-[N-(4-methylpyridin-2-yl)amino]pentanoic acid (177 mg, 0.852 mmol) was carried out as described in AAV 4, and removal of resin was carried out in accordance with AAV 5. After HPLC purification (10–80% in 30 min) and lyophilisation, a colourless powder was obtained (3.0 mg, 0.00542 mmol, 1.3%).

m.p. 103–109° C.; $^1$H-NMR (500 MHz, DMSO-$d_6$, 300 K) δ=8,81 (bs, 1H, NH—NH), 8.44 (bs, 1H, NH—NH), 8.25 (d, J=6.5 Hz, 1H, N—CH—CH), 7.74–7.77 (m, 4H, arom), 7.34 (s, 1H, N—C—CH), 7.21 (d, J=6.4 Hz, 1H, N—CH—CH), 6.06–6.07 (m, 1H, N—CH), 4.46–4.52 (m, 1H, CH—CH$_2$), 3.82–3.93 (m, 3H, NH—CH$_2$ and CH—CH$_2$), 3.47–3.57 (m, 2H, NCH$_2$CH$_2$), 3.30–3.40 (m, 2H, NCH$_2$CH$_2$), 2.94 (s, 3H, C—CH$_3$), 2.79–2.84 (m, 2H, CH$_2$—CO), 2.23–2.35 (m, 4H, NH—CH$_2$—CH$_2$—CH$_2$); MS (ESI) m/e 191.2 (8), 249.1 (100), 440.1 (30) [M+H]$^+$, 462.1 (8) [M+K]$^+$, 478.1 (10) [M+Na]$^+$, 901.0 (2) [2M+Na]$^+$, 917.1 (3) [2M+K]$^+$, 939.1 (4) [2M–H+Na+K]$^+$, 945.1 (4); HRMS for $C_{23}H_{30}N_5O_4$ [M+H]$^+$ 440.2273 (calc. 440.2298); analytical HPLC (5–90% in 30 min) $t_R$=14.69 min (92.7% purity at 220 nm)

Example 5a)

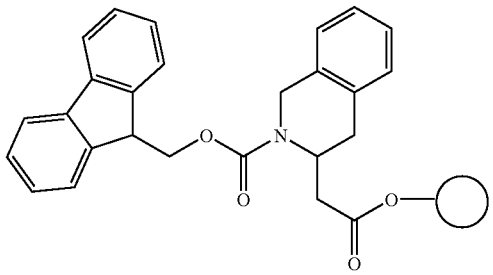

Resin-bound
Fmoc-1,2,3,4-tetrahydroisoquinolin-3(S)-ylacetic
acid 200 mg of trityl chloride-polystyrene resin (0.18 mmol theoretical loading) are washed in 1.5 ml of abs. DCM. A solution of 0.24 mmol of Fmoc-1,2,3,4-tetrahydroisoquinolin-3(S)-ylacetic acid and 0.6 mmol of DIPEA in 1.5 ml of abs. DCM is subsequently added to the resin, the mixture is shaken for 1.5 hours at room temperature, and 0.2 ml of methanol is then added. The mixture is washed with DCM (5×1.5 ml) and methanol (3×1.5 ml) and dried.

Example 5b)

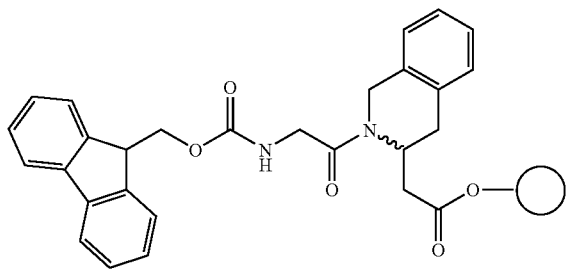

Resin-bound
Fmoc-Gly-1,2,3,4-tetrahydroisoquinolin-3-ylacetic
acid 0.072 mmol of A is washed with DMF (1×2 ml). The compound is subsequently deprotected twice using 20% of piperidine in DMF (2×2 ml), firstly for 5 minutes and then for 15 minutes, and washed with DMF (6×2 ml). An approximately 0.1M solution of 2.5 equivalents (based on the resin loading, 0.18 mmol) of Fmoc-glycine, 2.4 equivalents (0.17 mmol) of HATU and 30 equivalents (2.16 mmol) of sym-collidine in dry DMF is added to the resin-bound free amine, and the mixture is shaken at room temperature for 90 minutes. The reaction is terminated by washing in DMF (6×2 ml).

Example 5c)

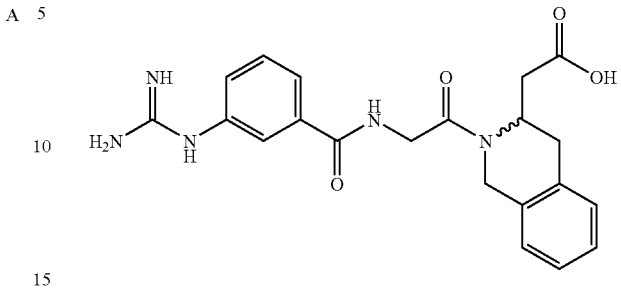

3-Guanidinobenzoylglycyl-1,2,3,4-tetrahydroisoquinolin-3-ylacetic acid 0.036 mmol of B is washed with DMF (1×1 ml). The compound is subsequently deprotected twice using 20% of piperidine in DMF (2×1 ml), firstly for 5 minutes and then for 15 minutes, and washed with DMF (6×1 ml). An approximately 0.1 M solution of 2.5 equivalents (based on the resin loading, 0.09 mmol) of Fmoc-3-aminobenzoic acid, 2.4 equivalents (0.086) of HATU and 30 equivalents (1.08) of sym-collidine in dry DMF is added to the resin-bound free amine, and the mixture is shaken at room temperature for 90 minutes. The mixture is washed with DMF (6×1 ml) and deprotected as described.

The resin is subsequently washed with anhydrous chloroform (3×1 ml), a solution of 0.36 mmol of N,N'-bis-BOC-1-guanylpyrazole in 0.4 ml of anhydrous chloroform is added, and the mixture is reacted in a heatable shaker at 50° C. After 20 hours, the resin is washed with DCM (6×1 ml). For removal from the resin with simultaneous removal of BOC, the resin is shaken with a 4.75:4.75:0.5 mixture of DCM, TFA and TIPS (3×1 ml), once for 1.5 hours, once for 30 minutes and once for 3 minutes, and filtered off The combined filtrates are evaporated, and the residue is lyophilised from tert-butanol/water. Purification using preparative HPLC gives 3-guanidinobenzoylglycyl-1,2,3,4-tetrahydroisoquinolin-3-ylacetic acid, trifluoroacetate.

RT=12.3 (10→90% ACN, 30 min)

MS (ESI): m/e=410.2 ([M+H]$^+$). $^1$H-NMR (1.3:1 ratio of the rotational isomers, * smaller rotational isomer signals, 500 MHz, DMSO-d$_6$) δ=12.39 (br. s, 1H, COOH), 9.95 (s, 1H, NH—$^{Ar}$C), 8.67 (t, J=5.4 Hz, 1H, NH—$^{Gly}$CH$_2$), 8.63* (t, J=5.4 Hz, 1H, NH—$^{Gly}$CH$_2$), 7.78 (d, J=7.8 Hz, 1H, $^{Ar}$C$^6$—H), 7.72 (s, 1H, $^{Ar}$C$^2$—H), 7.58 (s, 4H, $^{Gua}$N$_2$H$_4$), 7.53 (t, J=7.8 Hz, 1H, $^{Ar}$C$^5$—H), 7.39 (d, J=7.8 Hz, 1H, $^{Ar}$C$^4$—H), 7.17–7.25 (m, 4H, $^{Thiqu}$C$^{5,6,7,8}$—H), 5.11 (d, J=17.9 Hz, 1H, $^{Thiqu}$C$^1$—H$_2$), 5.01–5.02* (m, 1H, $^{Thiqu}$C$^3$—H), 4.82* (d, J=16.2 Hz, 1H, $^{Thiqu}$C$^1$—H$_2$), 4.73–4.75 (m, 1H, $^{Thiqu}$C$^3$—H), 4.55* (d, J=16.2 Hz, 1H, $^{Thiqu}$C$^1$—H$_2$), 4.44 (dd, J=16.4 Hz, J=5.4 Hz, 1H, $^{Gly}$CH$_2$), 4.19–4.29 (m, 3H, $^{Gly}$CH$_2$), 4.10 (d, J=17.9 Hz, 1H, $^{Thiqu}$C$^1$—H$_2$), 3.15 (dd, J=16.4 Hz, J=5.0 Hz, 1H CH$_2$CO$_2$H), 2.98* (dd, J=15.8 Hz, J=5.2 Hz, 1H, CH$_2$CO$_2$H), 2.74–2.79 (m, 2H, CH$_2$CO$_2$H), 2.41–2.51, 2.33–2.37, 2.16–2.21 (m, 4H, $^{Thiqu}$C$^4$—H$_2$).

Example 6

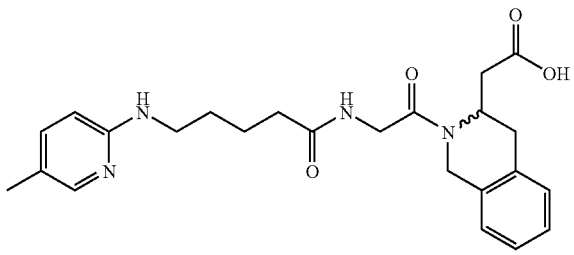

5-(4-Methylpyridin-2-ylamino)pentanoylglycyl-1,2,3,4-tetrahydroisoquinolin-3-ylacetic acid 0.036 mmol of B (obtainable as described in Example. 5b)) is washed with DMF (1×1 ml). The compound is subsequently deprotected twice using 20% of piperidine in DMF (2×1 ml), firstly for 5 minutes and then for 15 minutes, and washed with DMF (6×1 ml). The resin-bound free amine is shaken overnight at room temperature with an approximately 0.1 M solution of 2.5 equivalents (0.09 mmol) of 5-(N-(4-methylpyridin-2-yl)amino-pentanoic acid, 2.4 equivalents (0.086 mmol) of HATU and 30 equivalents (1.08 mmol) of collidine in absolute DMF. The mixture is washed with DMF and DCM. For removal from the solid phase, the washed resin is shaken with 1 ml of a mixture of DCM/trifluoroethanol/acetic acid (31/1), firstly for 90 minutes, then for 30 minutes and finally for 1 minute. Removal of the solvent and purification using preparative HPLC gives 5-(4-methylpyridin-2-ylamino)pentanoylglycyl-1,2,3,4-tetrahydroisoquinolin-3-ylacetic acid, trifluoroacetate.

RT=13.3 (10→90% ACN, 30 min)

MS (ESI): m/e=439.3 ([M+H]$^+$).

$^1$H-NMR (1.3:1 ratio of the rotational isomers, * smaller rotational isomer signals, 500 MHz, DMSO-d$_6$) δ=12.35 (br. s, 1H, COOH), 8.46 (br. s, 1H, NH—CH$_2$), 7.93–7.97 (m, 1H, NH—$^{Gly}$CH$_2$), 7.78 (d, J=6.5 Hz, 1H, $^{Pyr}$C$^6$—H), 7.14–7.22 (m, 4H, $^{Thiqu}$C$^{5,6,7,8}$—H), 6.81 (s, 1H, $^{Pyr}$C$^3$—H), 6.69 (d, J=6.5 Hz, 1H, $^{Pyr}$C$^5$—H), 5.08 (d, J=17.9 Hz, 1H, $^{Thiqu}$C$^1$—H$_2$), 4.97–5.01* (m, 1H, $^{Thiqu}$C$^3$—H), 4.71* (d, J=16.2 Hz, 1H, $^{Thiqu}$C$^1$—H$_2$ 4.59–4.63 (m, 1H, $^{Thiqu}$C$^3$—H), 4.47* (d, J=16.2 Hz, 1H, $^{Thiqu}$C$^1$—H$_2$) (dd, J=16.7 Hz, J=5.5 Hz, 1H, $^{Gly}$CH$_2$), 4.04–4.08 (m, 3H, $^{Gly}$CH$_2$, $^{Thiqu}$C$^1$—H$_2$), 3.97* (dd, J=16.9 Hz, J=5.4 Hz, 1H, $^{Gly}$CH$_2$), 3.27 (m, 2H, NH—CH$_2$), 3.11 (dd, J=16.2 Hz, J=5.3 Hz, 1H, CH$_2$CO$_2$H), 2.95* (dd, J=15.7 Hz, J=5.4 Hz, 1H, CH$_2$CO$_2$H), 2.62–2.77 (m, 2H, CH$_2$CO$_2$H), 2.34–2.44 (m, 3H, $^{Thiqu}$C$^4$—H$_2$) 2.31 (s, 3H, CH$_3$), 2.12–2.21 (m, 3H, $^{Thiqu}$C$^4$—H$_4$, CH$_2$—CH$_2$—CO), 1.58 (s, 4H, (CH$_2$)$_2$—CH$_2$—CO).

The other compounds of the formula I, in particular the compounds of the formulae I1 to I36, can be obtained analogously using the corresponding precursors.

The examples below relate to pharmaceutical preparations:

Example A

Injection Vials

A solution of 100 g of an active ingredient of the formula I and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

Example B

Suppositories

A mixture of 20 g of an active ingredient of the formula I is melted with 100 g of soya lecithin and 1400 g of cocoa butter, poured into moulds and allowed to cool. Each suppository contains 20 mg of active ingredient.

Example C

Solution

A solution is prepared from 1 g of an active ingredient of the formula I, 9.38 g of NaH$_2$PO$_4$.2 H$_2$O, 28.48 g of Na$_2$HPO$_4$.12 H$_2$O and 0.1 g of benzalkonium chloride in 940 ml of bidistilled water. The pH is adjusted to 6.8, and the solution is made up to 1 l and sterilised by irradiation. This solution can be used in the form of eye drops:

Example D

Ointment 500 mg of an active ingredient of the formula I are mixed with 99.5 g of Vaseline under aseptic conditions.

Example E

Tablets

A mixture of 1 kg of active ingredient of the formula I, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

Example F

Coated Tablets

Tablets are pressed analogously to Example E and subsequently coated in a conventional manner with a coating of sucrose, potato starch, talc, tragacanth and dye.

Example G

Capsules 2 kg of active ingredient of the formula I are introduced into hard gelatine capsules in a conventional manner in such a way that each capsule contains 20 mg of the active ingredient.

Example H

Ampoules

A solution of 1 kg of active ingredient of the formula I in 60 of bidistilled water is sterile filtered, transferred into ampoules, lyophilised under sterile conditions and sealed under sterile conditions. Each ampoule contains 10 mg of active ingredient.

Example I

Inhalation Spray 14 g of active ingredient of the formula I are dissolved in 10 l of isotonic NaCl solution, and the solution is transferred into commercially available spray containers with a pump mechanism. The solution can be sprayed into the mouth or nose. One spray shot (about 0.1 ml) corresponds to a dose of about 0.14 mg.

The invention claimed is:

1. A compound of the formula I:

in which
X is H, —C(=NR$^3$)—NHR$^4$ or Het,

Y is —(CH$_2$)$_m$-,
Z is NH or CH$_2$,
R$^1$ and R$^5$ are each, independently of one another, H, A, OH, OA, arylalkyl, Hal, —CO—A, CN, NO$_2$, NHR$^3$, COOA, COOH, SO$_2$A, CF$_3$ or OCF$_3$,
R$^2$ is in each case, independently of the others, H or A,
R$^3$ and R$^4$ are each, independently of one another, H, A, —CO—A, NO$_2$ or CN,
A is alkyl having 1–6 carbon atoms,
m is 0, 1, 2, 3, 4, 5 or 6,
n and p are, independently of one another, 1, 2 or 3;
or a physiologically acceptable salt or solvate thereof.

2. A compound of the formula I of claim 1, wherein A is methyl, ethyl, isopropyl, n-propyl, n-butyl, isobutyl, sec-butyl or tert-butyl.

3. A compound of the formula I of claim 1, wherein Het is 4-methylpyridin-2-yl, pyridin-2-yl, pyrimidin-2-yl, imidazol-2-yl, benzimidazol-2-yl or a hydrogenated group thereof.

4. A compound of the formula I of claim 1, wherein R$^1$ and R$^5$, independently of one another, are H, A, CN, NO$_2$, Hal or —COA.

5. A compound of the formula I of claim 1, wherein R$^2$ H or A.

6. A compound of the formula I of claim 1, wherein R$^3$ and R$^4$, independently of one another, are H or —COA.

7. A compound of the formula I of claim 1, wherein X is H, —C(=NH)—NH$_2$, —C(=N-methyl)-NH$_2$, 4-methylpyridin-2-yl, pyridin-2-yl, pyrimidin-2-yl, imidazol-2-yl, benzimidazol-2-yl or a hydrogenated group thereof.

8. A compound of the formula I of claim 1, wherein Y is —(CH$_2$)$_m$- or

9. A compound of the formula I of claim 1, wherein n and p, independently of one another, are 1 or 2.

10. A compound of the formula I of claim 1, wherein m is 0, 2 or 4.

11. A compound of the formula I of claim 1, which is of one of the following formulae I1 to I36:

-continued
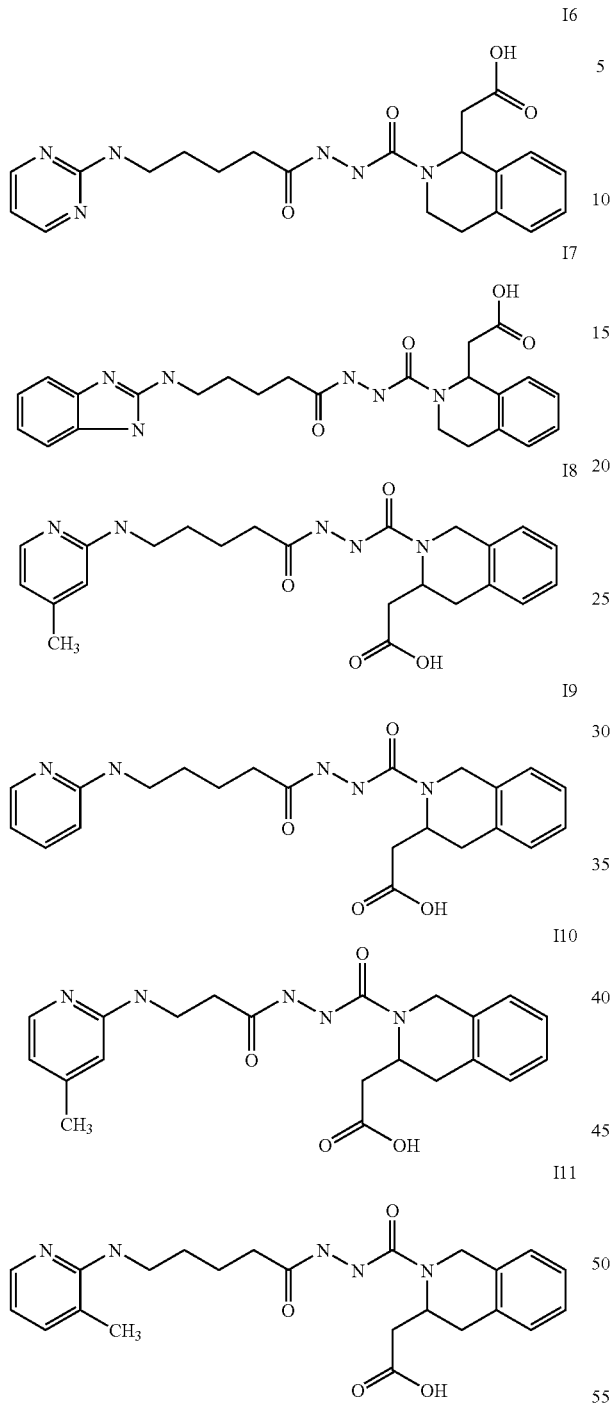
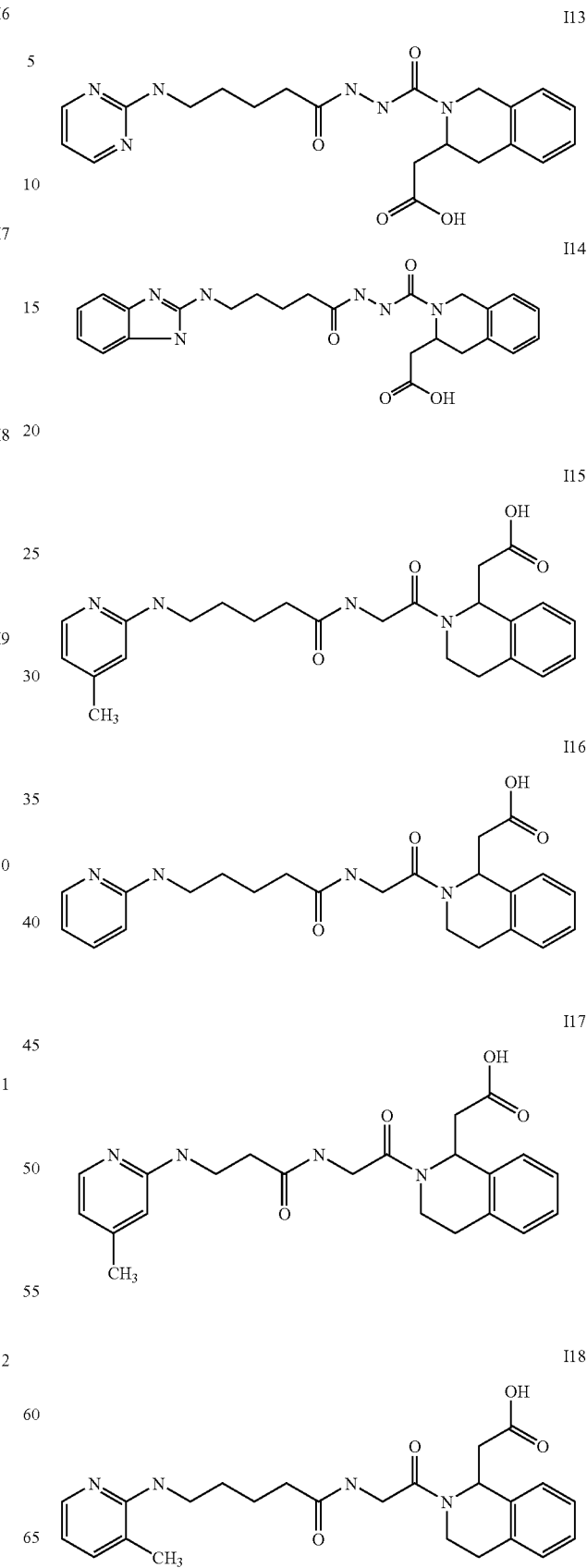

35

-continued

I19, I20, I21, I22, I23, I24, I25

36

-continued

I26, I27, I28, I29, I30, I31

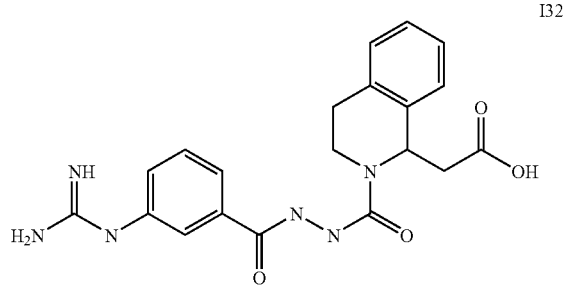

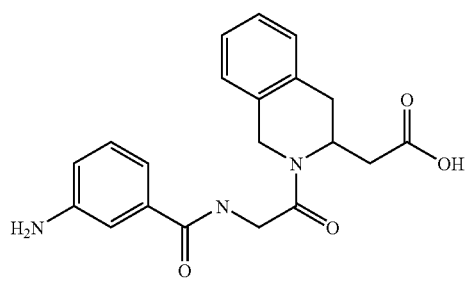

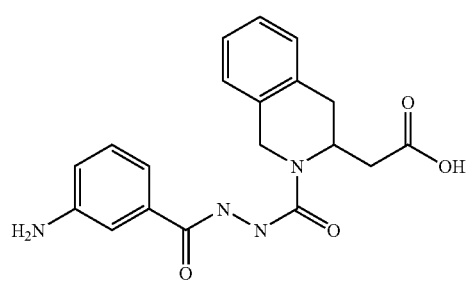

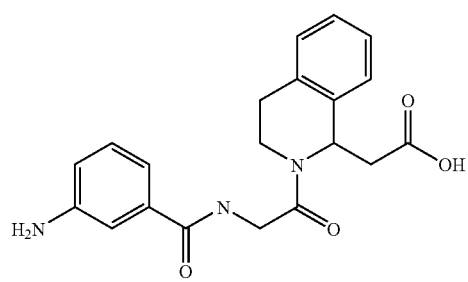

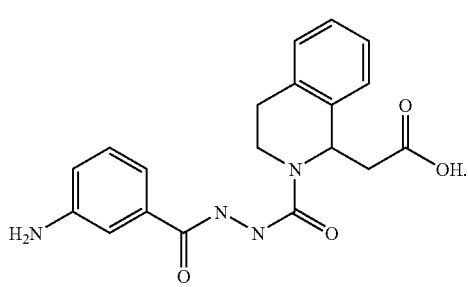

12. A method for preparing a compound of the formula I of claim 1, which comprises:

a) reacting a compound of the formula II

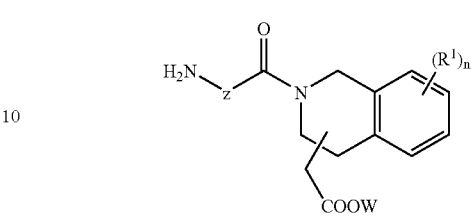

in which Z, $R^1$ and n are as defined above, and W is a conventional protecting group or a solid phase used in peptide chemistry, with a compound of the formula III

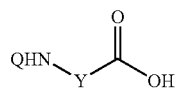

in which Y is as defined above, and Q is a suitable protecting group or Het, in the presence of a condensing agent, removing at least one protecting group and/or the solid phase, and, optionally, where Q as protecting group is removed, reacting the resultant product with a guanyl compound and, optionally, removing any remaining protecting groups and/or the solid phase, or b) liberating a compound of the formula I from a functional derivative of a compound of the formula I by treatment with a solvolyzing or hydrogenolyzing agent, and/or c) converting a basic or acidic compound of the formula I into one of its salts by treatment with an acid or base.

13. A pharmaceutical composition comprising a compound of the formula I of claim 1 or a physiologically acceptable salt or solvate thereof and at least one solid, liquid and/or semi-liquid excipient or adjuvant.

14. A composition of claim 13 comprising an amount of the compound of the formula I effective to provide integrin inhibitor activity.

15. A method for preparing a composition of claim 13 which comprises formulating a compound of the formula I with at least one solid, liquid and/or semi-liquid excipient or adjuvant.

16. A method for treating thromboses, cardiac infarction, coronary heart disease, arteriosclerosis, inflammation, tumours, osteoporosis, an infection or restenosis after angioplasty, which comprises administering to a patient in need thereof a compound of formula I of claim 1 or a physiologically acceptable salt or solvate thereof.

* * * * *